(12) United States Patent
Brady et al.

(10) Patent No.: US 9,445,889 B2
(45) Date of Patent: Sep. 20, 2016

(54) CAPSULAR MEMBRANE IMPLANTS TO INCREASE ACCOMMODATIVE AMPLITUDE

(75) Inventors: Daniel G. Brady, San Juan Capistrano, CA (US); Zsolt Bor, San Clemente, CA (US); Edward Geraghty, Rancho Santa Margarita, CA (US); Brooke C. Basinger, Long Beach, CA (US); Carina R. Reisin, Tustin, CA (US); Douglas S. Cali, Mission Viejo, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 446 days.

(21) Appl. No.: 13/043,178

(22) Filed: Mar. 8, 2011

(65) Prior Publication Data
US 2012/0059465 A1 Mar. 8, 2012

Related U.S. Application Data

(63) Continuation-in-part of application No. 12/570,780, filed on Sep. 30, 2009, now Pat. No. 8,518,028.

(51) Int. Cl.
*A61F 9/008* (2006.01)
*A61F 2/14* (2006.01)
(Continued)

(52) U.S. Cl.
CPC ................ *A61F 2/14* (2013.01); *A61F 9/008* (2013.01); *A61F 9/00736* (2013.01);
(Continued)

(58) Field of Classification Search
CPC ..................... A61B 2/1635; A61B 2250/0053; A61B 2/1613; A61B 2/1648
USPC ............................................................ 606/1
See application file for complete search history.

(56) References Cited

U.S. PATENT DOCUMENTS

| 4,134,161 A | 1/1979 | Bayers |
| 4,136,466 A | 1/1979 | Wrue |

(Continued)

FOREIGN PATENT DOCUMENTS

| DE | 102006036800 A1 | 2/2008 |
| EP | 94158 A1 | 11/1983 |

(Continued)

OTHER PUBLICATIONS

Chan B.P., et al., "Effects of Photochemical Crosslinking on the Microstructure of Collagen and a Feasibility Study on Controlled Protein Release," Acta Biomaterialia , 2008, vol. 4 (6), pp. 1627-1636.

(Continued)

*Primary Examiner* — Aaron Roane
(74) *Attorney, Agent, or Firm* — Abbott Medical Optics Inc.

(57) ABSTRACT

A support is coupled to the lens capsule to increase accommodation. The support may be adjustable, such that patient refraction and accommodation can be adjusted following surgery. The support may comprise rigidity sufficient to decrease radial movement of the intermediate portion of the lens capsule. The support can be placed on the intermediate portion to decrease radial movement of the intermediate portion of the lens capsule and increase radial stretching of an outer portion of the lens capsule extending between the zonules and the intermediate portion coupled to the support, such that the amount of accommodation of the eye is increased. The support may comprise a biocompatible material capable of stable coupling to the lens capsule following implantation, such that the far vision refraction and accommodation of the eye can be stable following surgery.

16 Claims, 19 Drawing Sheets

(51) Int. Cl.
*A61F 9/007* (2006.01)
*A61F 2/16* (2006.01)

(52) U.S. Cl.
CPC ......... *A61F 2/1624* (2013.01); *A61F 9/00838* (2013.01); *A61F 2009/0087* (2013.01); *A61F 2009/00889* (2013.01); *A61F 2009/00895* (2013.01)

(56) References Cited

U.S. PATENT DOCUMENTS

| | | | |
|---|---|---|---|
| 4,219,721 | A | 8/1980 | Kamen et al. |
| 4,403,354 | A | 9/1983 | Rainin |
| 4,435,855 | A | 3/1984 | Pannu |
| 4,443,441 | A | 4/1984 | Galin |
| 4,463,457 | A | 8/1984 | Kelman |
| 4,559,942 | A | 12/1985 | Eisenberg |
| 4,575,373 | A | 3/1986 | Johnson |
| 4,585,456 | A | 4/1986 | Blackmore |
| 4,617,023 | A | 10/1986 | Peyman |
| 4,642,113 | A | 2/1987 | Dubroff |
| 4,661,109 | A | 4/1987 | White |
| 4,662,882 | A | 5/1987 | Hoffer |
| 4,666,445 | A | 5/1987 | Tillay |
| 4,676,793 | A | 6/1987 | Bechert, II |
| 4,681,585 | A | 7/1987 | Sayano et al. |
| 4,685,921 | A | 8/1987 | Peyman |
| 4,685,922 | A | 8/1987 | Peyman |
| 4,687,485 | A | 8/1987 | Lim et al. |
| 4,704,016 | A * | 11/1987 | de Carle ................. 351/159.41 |
| 4,764,930 | A | 8/1988 | Bille et al. |
| 4,781,718 | A | 11/1988 | Lindstrom |
| 4,834,753 | A | 5/1989 | Sulc et al. |
| 4,872,876 | A | 10/1989 | Smith |
| 4,946,470 | A | 8/1990 | Sulc et al. |
| 5,108,429 | A | 4/1992 | Wiley |
| 5,147,395 | A | 9/1992 | Willis |
| 5,217,491 | A | 6/1993 | Vanderbilt |
| 5,225,858 | A | 7/1993 | Portney |
| 5,259,813 | A | 11/1993 | Abthoff et al. |
| 5,269,813 | A | 12/1993 | Yoshida et al. |
| 5,288,293 | A | 2/1994 | O'donnell, Jr. |
| 5,571,177 | A | 11/1996 | Deacon et al. |
| 5,713,892 | A | 2/1998 | Shimmick |
| 5,728,156 | A | 3/1998 | Gupta et al. |
| 5,984,962 | A | 11/1999 | Anello et al. |
| 5,993,438 | A | 11/1999 | Juhasz et al. |
| 6,210,005 | B1 | 4/2001 | Portney |
| 6,887,083 | B2 | 5/2005 | Umeyama et al. |
| 6,923,955 | B2 | 8/2005 | Till et al. |
| 7,044,945 | B2 | 5/2006 | Sand |
| 2001/0010019 | A1 | 7/2001 | Schachar |
| 2002/0103478 | A1 | 8/2002 | Gwon et al. |
| 2003/0028248 | A1 | 2/2003 | Shahinpoor et al. |
| 2004/0082993 | A1 | 4/2004 | Woods |
| 2004/0111153 | A1* | 6/2004 | Woods et al. ................ 623/6.37 |
| 2004/0153150 | A1 | 8/2004 | Ghazizadeh et al. |
| 2004/0199149 | A1 | 10/2004 | Myers et al. |
| 2004/0243111 | A1 | 12/2004 | Bendett et al. |
| 2006/0253196 | A1 | 11/2006 | Woods |
| 2006/0265058 | A1 | 11/2006 | Silvestrini |
| 2007/0185475 | A1 | 8/2007 | Frey et al. |
| 2008/0140192 | A1 | 6/2008 | Humayun et al. |
| 2008/0161913 | A1 | 7/2008 | Brady et al. |
| 2008/0161914 | A1* | 7/2008 | Brady et al. ................. 623/6.46 |
| 2010/0292678 | A1 | 11/2010 | Frey et al. |

FOREIGN PATENT DOCUMENTS

| | | | |
|---|---|---|---|
| EP | 0278724 | A2 | 8/1988 |
| EP | 336318 | A2 | 10/1989 |
| EP | 478929 | A1 | 4/1992 |
| SU | 1424828 | A1 | 9/1988 |
| WO | 8701931 | A1 | 4/1987 |
| WO | 9007914 | A1 | 7/1990 |
| WO | WO0182815 | A1 | 11/2001 |
| WO | WO02071976 | A2 | 9/2002 |
| WO | WO03057081 | A2 | 7/2003 |
| WO | 2004039295 | A1 | 5/2004 |
| WO | WO2004039395 | A1 | 5/2004 |
| WO | WO2004082542 | A2 | 9/2004 |
| WO | WO2007084602 | A2 | 7/2007 |
| WO | WO2010059847 | A1 | 5/2010 |

OTHER PUBLICATIONS

Glasser A., "Accommodation" in: Encyclopedia of Eye, vol. 1, Dartt D.A., ed., Oxford Academic Press, 2010, pp. 8-17.

Glasser A., et al., "Accommodation and Presbyopia" in: Adler's Physiology of the Eye, 10th Edition, Kaufman P.L., et al., Eds., Mosby, 2002, pp. 195-233.

Glasser A., "Physiology of Accommodation and Presbyopia" in: Surgery for Hyperopia, Sher N.A., Ed., Slack, Inc., 2004, pp. 11-21.

Glasser A., "The Helmholtz Mechanism of Accommodation" in: Hyperopia and Presbyopia, Chapter 3, Tsubota K., et al., eds., Marcel Dekker, Inc., 2003, pp. 27-47.

Hans Pau et al., "Cortical and Subcapsular Cataracts: Significance of Physical Forces", 2006, 220, 1-5.

Henderson B.A., et al., "Stepwise Approach to Establishing an Ophthalmology Wet Laboratory," Journal of Cataract & Refractive Surgery , 2009, vol. 35 (6), pp. 1121-1128.

Hovanesian J.A., et al., "Cataract wound Closure with a Polymerizing Liquid Hydrogel Ocular bandage," Journal of Cataract & Refractive Surgery , 2009, vol. 35 (5), pp. 912-916.

Hovanesian J.A., et al., "Watertight Cataract Incision Closure Using Fibrin Tissue Adhesive," Journal of Cataract & Refractive Surgery , 2007, vol. 33, pp. 1461-1463.

International Search Report for Application No. PCT/US2010/050752, mailed on Mar. 22, 2011, 5 pages.

Menabeuoni L., et al., "Laser-Assisted Corneal Welding in Cataract Surgery: Retrospective Study," Journal of Cataract and Refractive Surgery, 2007, vol. 33 (9), pp. 1608-1612.

Pandey S.K., et al., "Creating Cataracts of Varying Hardness to Practice Extracapsular Cataract Extraction and Phacoemulsification," Journal of Cataract & Refractive Surgery , 2000, vol. 26 (3), pp. 322-329.

Pandey S.K., et al., "Induction of Cataracts of Varying Degrees of Hardness in Human Eyes Obtained Postmortem for Cataract Surgeon Training," American Journal of Ophthalmology, 2000, vol. 129 (4), pp. 557-558.

Ripken T., et al., "Fs-Laser Induced Elasticity Changes to Improve Presbyopic Lens Accommodation," Graefe's Archive for Clinical and Experimental Ophthalmology, 2008, vol. 246 (6), pp. 897-906.

Shentu X., et al., "Combined Microwave Energy and Fixative Agent for Cataract Induction in Pig Eyes," Journal of Cataract & Refractive Surgery , 2009, vol. 35 (7), pp. 1150-1155.

Sugiura T., et al., "Creating Cataract in a Pig Eye," Journal of Cataract & Refractive Surgery , 1999, vol. 25, pp. 615-621.

Tseng Y., et al., "How Actin Crosslinking and Bundling Proteins Cooperate to Generate an Enhanced Cell Mechanical Response," Biochemical and Biophysical Research Communications, 2005, vol. 334, pp. 183-192.

Weeber H.A., et al., "The Role of the Capsular Bag in Accommodation" in: Current Aspects of Human Accommodation II, Guthoff R., eds., Heidelberg, Kaden Verlag, 2003, pp. 119-126.

Ayaki et al., "Histopathologic study of after cataract in the pseudophakic rabbit eye using out-of-the-bag fixation, ," Nippon Ganka Gakkai Zasshi, pp. 553-558, 1990, vol. 94 (6).

Ayaki et al, "Histopathologic study of after-cataract in the pseudophakic rabbit eye using in-the-bag fixation, ," Nippon Ganka Gakkai Zasshi , pp. 559-565, 1990, vol. 94 (6).

Biedner B, "Subconjunctival dislocation of intraocular lens implant," Am J Ophthalmol, pp. 265-266, 1977, vol. 84 (2).

Bloom et al, "Scleral fixation suture for dislocated posterior chamber intraocular lens," Ophthalmic Surg, pp. 851-854, 1990, vol. 21 (12).

Bowman et al, "Noninvasive repositioning of a posterior chamber intraocular lens following pupillary capture, ," J Cataract Refract Sur, pp. 843-847, 1991, vol. 17 (6).

(56) References Cited

OTHER PUBLICATIONS

Chan, "An improved technique for management of dislocated posterior chamber implants," Ophthalmology, pp. 51-57, 1992, vol. 99 (1).
Corcoran, "Spontaneous repositioning of a dislocated Medallion intraocular lens," J Am lntraocul Implant Soc, pp. 598-599, 1985, vol. 11 (6).
Flynn et al., "Management of subluxated and posteriorly dislocated intraocular lenses using pars plana vitrectomy instrumentation," J Cataract Refract Surg, , pp. 51-56, 1990, vol. 16 (1).
Moretsky, "Suture fixation technique for subluxated posterior chamber IOL through stab wound incision," J Am Intraocul Implant Soc Fall , pp. 477-480, 1984, vol. 10 (4).
Nabors et al., "Ciliary sulcus suturing of a posterior chamber intraocular lens," Ophthalmic Surg, pp. 263-265, 1990, vol. 21 (4).
Neumann et al., "Complications associated with STAAR silicone implants," J Cataract Refract Surg, pp. 653-656, 1987, vol. 13 (6).
Nevyas et al., "A YAG laser technique to facilitate removal of posterior chamber intraocular-lenses from the capsular bag," J Cataract Refract Surg , pp. 201-204, 1987, vol. 13 (2).
Poley et al., "A closed technique for repositioning dislocated iris plane lenses," J Am Intraocul Implant Soc, pp. 316-320, 1979, vol. 5 (4).
Praeger, "Praeger micro irrigating hook intraocular lens implantation," Ophthalmic Surg, pp. 30-32, 1979, vol. 10 (7).
Smiddy, "Dislocated posterior chamber intraocular lens A new technique of management," Arch Ophthalmol, pp. 1678-1680, 1989, vol. 107 (11).
Smiddy et al., "Management of dislocated posterior chamber intraocular lenses," Opthalmology Jun, pp. 889-894, 1991, vol. 98 (6).
Stark et al., "Management of posteriorally dislocated intraocular lenses," Ophthalmic Surg, pp. 495-497, 1980, vol. 11 (8).
Wand et al, "Thymoxamine hydrochloride:an alpha-adrenergic blocker ," Sury Ophthalmol , pp. 75-84, 1980, vol. 25 (2).
International Preliminary Report on Patentability and Written Opinion for Application No. PCT/US2010/050752, mailed on Apr. 3, 2012, 9 pages.
International Search Report and Written Opinion for Application No. PCT/US2012/028095, mailed on Jun. 19, 2012, 11 pages.
Flynn H.W., "Pars Plana Vitrectomy in the Management of Subluxed and Posteriorly Dislocated Intraocular Lenses," Graefe's Archive for Clinical and Experimental Ophthalmology, 1987, vol. 225 (3), pp. 169-172.
Friedberg M.A., et al., "A New Technique for Repositioning and Fixating a Dislocated Intraocular Lens," Archives of Ophthalmology, 1992, vol. 110 (3), pp. 413-415.
International Search Report and Written Opinion for Application No. PCT/US2012/028090, mailed on Sep. 25, 2012, 19 Pages.
International Search Report and Written Opinion, mailed Jan. 14, 2010, and International Preliminary Report on Patentability, mailed Mar. 29, 2011, for Application No. PCT/US2009/058321, 11 pages.
International Search Report for Application No. PCT/US94/06403, mailed on Sep. 20, 1994, 4 pages.
Lyons C.J., et al., "Report of a Repositioned Posteriorly Dislocated Intraocular Lens via Pars Plicata Sclerotomy," Journal of Cataract Refractive Surgery, 1990, vol. 16 (4), pp. 509-511.
Partial International Search Report for Application No. PCT/US2012/028090, mailed May 29, 2012, 6 pages.
Sternberg P., et al., "Treatment of Dislocated Posterior Chamber Intraocular Lenses," Archives of Ophthalmology, 1986, vol. 104 (9), pp. 1391-1393.

\* cited by examiner

FIG. 2B  FIG. 2A-1

CAPSULAR MEMBRANE IMPLANTS TO INCREASE ACCOMMODATIVE AMPLITUDE

This application is a continuation-in-part of and claims priority to U.S. application Ser. No. 12/570,780, filed on Sep. 30, 2009, which is hereby incorporated by reference in its entirety for all purposes as if fully set forth herein.

BACKGROUND OF THE INVENTION

The present invention relates to accommodation of the eye and treatment of presbyopia.

The eye has a cornea and a lens. The cornea and lens focus light on a retina such that a person can perceive the image with the retina located on the back of the eye. When the image on the retina is focused, the image appears sharp to the patient. However, when the image is out of focus, the image appears blurred. An eyeglass prescription to correct far vision of the eye can be referred to clinically as a refraction of the eye, and the measured refraction of the eye can include a sphere, a cylinder and an axis of the cylinder. Corrective lenses can be prescribed based on the refraction of the eye such that optical errors of the eye such as nearsightedness, also referred to as myopia, and farsightedness, also referred to as hyperopia, can be corrected. Nearsightedness corresponds to an eye having too much optical power such that objects near the eye appear in focus and distant objects appear blurred. With a nearsighted eye, lenses having negative optical power can be used to correct the refractive error of the eye. Farsightedness can refer to an eye not having enough optical power such that positive lenses placed in front of the farsighted eye can correct near vision.

In the normal healthy eye, the lens of the eye can accommodate to both near and far distances of the object viewed such that the image of the object is focused on the retina and remains sharp to the patient. For far vision, the ciliary muscles of the eye can relax and adjust the lens to focus on a far object that may be several meters away. For near vision, the ciliary muscles of the eye can constrict and adjust the lens to focus on a near object. The near object can be located at a distance suitable for reading, for example. The eye can accommodate with movement of the lens to focus on objects at intermediate distances.

With age the accommodation of the eye can decrease such that a person with good distance vision may benefit from lenses to see near objects clearly. The decrease of accommodation of the eye corresponding to presbyopia may be related to a stiffer crystalline lens that decreases the accommodative amplitude of the lens of the eye in at least some instances. People who are near sighted and wear glasses for distance vision may find glasses that correct sight for far vision do not provide near vision correction in at least some instance. This loss of accommodation of the eye can be referred to as presbyopia.

Although many forms of optical correction and devices have been proposed to treat presbyopia, at least some of these approaches have one or more deficiencies such that the prior correction of presbyopia may be less than ideal in at least some instances. Although reading glasses can be effective when worn, in at least some instances a person may not have reading glasses and need near vision. Also, switching from near vision to far vision with reading glasses can be less than ideal in at least some instances. Although bifocals are available, such corrective lenses may provide less than ideal results in at least some instances such as when a person engages in water sport or sweats such that the correction of the lenses can be at least partially distorted.

Although it has been proposed to treat tissue with energy to correct presbyopia, such tissue treatments can be more invasive than would be ideal and may be somewhat unstable in at least some instances. For example, although it has been proposed to reduce the stiffness of the natural crystalline lens through laser treatment allowing for improvement in the ability of the crystalline lens to change power, it may be possible to create a cataract in at least some instances. Also, treatment of the lens can potentially result in changes in refraction of the eye such that the refraction and uncorrected vision of the eye may be less than ideal in at least some instances. Further, at least some tissue treatments can be unstable in at least some instances such that the treatment may result in no more than a temporary change to the eye in at least some instances. For example, electrocautery of the lens capsule may be related to decreased thickness of the lens capsule that may contribute to cataract formation and may be related to unstable refraction of the eye, in at least some instances.

Patients who receive intra ocular lenses (hereinafter "IOLs") may have no effective accommodation, and may be considered presbyopic in at least some instances. For example, although IOL surgery to replace a cataract of the natural lens of the eye can be effective in restoring vision of the patient, such patients cannot accommodate effectively in at least some instances. Also, IOL surgery can be somewhat variable in at least some instances, such that the refraction of the eye with the IOL can be less than ideal in at least some instances.

Although multifocal lenses have been proposed, such lenses can result in undesirable visual phenomenon (hereinafter "dysphotopsia") in at least some instances. Although multifocal lenses may provide a first optical correction for near vision and a second optical power for distance vision, the light rays having the second optical power for near vision may provide visual phenomenon such as halos for a distant object, for example when the patient views a distant object.

One promising approach to treat patients who have received IOLs for cataract surgery has been to introduce an accommodating IOL. However, such IOLs have resulted in less accommodation than would be ideal and can be more difficult to implant in at least some instances. Also, recovery time of accommodating IOLs may be longer than a non-accommodating IOL, in at least some instances. Also, the accommodative abilities may not be restored as would be ideal in at least some instances. Though vision may be improved, the degree of improvement can vary among patients and may be less predictable than would be ideal in at least some instances.

In light of the above, it would be desirable to provide improved methods and apparatus for increased accommodation of the eye that overcome one or more of the above mentioned limitations of the prior approaches. Ideally such methods and apparatus would restore accommodation to provide near and far vision correction with reduced side effects.

SUMMARY OF THE INVENTION

Embodiments of the present invention provide improved treatment so as to improve patient accommodation with the natural lens of the eye or an IOL, or combinations thereof. In many embodiments, movement of an intermediate portion of the lens capsule is decreased, for example inhibited, with a support coupled to the intermediate portion so as to increase accommodation. The support may be adjustable, such that patient refraction and accommodation can be adjusted following surgery. The support may comprise rigidity sufficient to decrease radial movement of the intermediate portion of the lens capsule such that accommodation of the eye can be increased and presbyopia mitigated. The support may comprise a biocompatible material capable of stable coupling to the lens capsule following implantation, such that the far distance refraction and accommodation of the eye can be stable following surgery. The support can be coupled to the lens capsule at an intermediate portion of the lens capsule away from the pupil center, such that patient vision can be maintained. The intermediate portion of the lens capsule coupled to the support may be located between the central optical potion of the lens capsule and an elastic peripheral portion of the lens capsule attached to zonules of the eye. As the support can be located away from the central optically used portion of the lens, optics of the eye and vision can be preserved, and the support may comprise an opaque material. The stiffening support can be placed on the intermediate portion to decrease radial stretching and movement of the intermediate portion of the lens capsule. The support can extend substantially around the central portion and may comprise an annular structure such as a ring or oval annular structure, so as to decrease circumferential stretching of the annular support, such that radial movement of the intermediate portion of the lens capsule corresponding to circumferential stretching of the intermediate portion of the lens capsule can be decreased. The stiffening support can increase radial stretching of an outer portion of the lens capsule extending between the zonules and the intermediate portion coupled to the support, such that the accommodative forces of the eye and the amount of accommodation of the eye can be increased. The intermediate portion of the lens capsule coupled to the support may comprise the anterior lens capsule, or the posterior lens capsule, or combinations thereof.

The support can be shaped and coupled to the intermediate portion of the lens capsule in many ways. The support may be coupled to the intermediate portion with one or more of an adhesive, thermal bonding, mechanical coupling, clamping or sutures. The support may be adhered to the intermediate portion with a biocompatible adhesive. Alternatively or in combination, the support may comprise a channel sized to receive the intermediate portion of the lens capsule. The support may comprise one or more of filaments, fibers, a flexible material, a shape memory material, a bendable material or a mesh material. The support may comprise a first folded elongate profile configuration for insertion into the eye through a narrow incision and a second wide profile configuration to improve accommodation when placed on the lens capsule, such that the support extends substantially along the intermediate portion of the lens capsule. For example, the elongate configuration may comprise a folded and/or flexible configuration sized to fit within a lumen of an insertion device for delivery into the anterior chamber through an incision no more than about 2 mm across, and the expanded configuration may comprise an annular shape, for example a C shaped ring configuration, when positioned on the intermediate portion of the capsule.

The lens may comprise the natural lens of the eye or an artificial lens such as an accommodative IOL. When used to increase accommodation of the natural lens of the eye, the support can be positioned on an outer anterior surface of the anterior lens capsule away from the subcapsular epithelium so as to decrease invasiveness of the procedure. With placement on the anterior surface of the anterior capsule, the support can increase curvature of the central portion of the capsule and central portion of the natural lens during accommodation such that the amount of accommodation of the eye is increased. The support can be used with one or more additional treatments of the eye such as capsulorhexis, laser treatment or an artificial and accommodative IOL. The accommodative IOL may comprise a moveable component such as a haptic that moves the artificial lens to accommodate, or a flexible artificial lens that bends to accommodate, or combinations thereof. The accommodation can be increased with increased force to the IOL from the supported and/or stiffened intermediate portion of the lens capsule.

The support coupled to the intermediate portion to decrease radial movement can increase radial stretching of an outer portion of the lens capsule, such that the accommodative forces of the eye and the amount of accommodation of the eye are increased. The stretched outer portion of the lens capsule can extend from the intermediate portion coupled to the support to the peripheral portion coupled to the zonules. The support coupled to the intermediate portion can be sized or adjusted such that radial stretching of the outer portion is increased when the ciliary muscles of the eye relax and tension of the zonules moves the peripheral portion of the lens capsule radially outward and away from the intermediate portion having the decreased radial movement. As the amount of stretching of the outer portion can be increased, the amount of force to move the peripheral portion inward can be increased substantially when the eye accommodates.

The support can be adjustable, such that one or more of the accommodation or the far vision refraction of the eye can be adjusted with the support. The stiffness of the support can be adjusted to adjust amount of accommodation. The stiffness of the support may be increased to increase accommodation of the eye. The dimension across the support can be adjusted so as to adjust the refraction of the eye, and an increase in the dimension may correspond to decreased optical power of the eye and a decrease in the dimension may increase the optical power of the eye.

In a first aspect, embodiments provide a method of treating an eye. The eye has a lens and a capsule. A support is placed on an intermediate portion of the capsule to decrease radial movement of the intermediate portion and increase an amount of accommodation of the eye.

In many embodiments, a peripheral portion of the lens capsule is coupled to the intermediate portion of the lens capsule, and radial movement of the peripheral portion is increased when the support is coupled to the intermediate portion.

In many embodiments, a central portion of the lens capsule is coupled to the peripheral portion, and an anterior movement of the central portion is increased when the intermediate portion is coupled to the support.

In many embodiments, the decreased radial movement comprises one or more of a stretching, a bending, a flexing, a translation or a rotation of the intermediate portion.

In many embodiments, the eye has a first amount of accommodation prior to placement of the support on the eye and a second amount of accommodation when the support is placed on the intermediate portion of the capsule, and the second amount is greater than the first amount.

In many embodiments, the capsule comprises one or more of an anterior capsule or a posterior capsule.

In many embodiments, the portion comprises an intermediate portion of the lens capsule located between a peripheral portion of the lens capsule and a central portion of the lens capsule. The peripheral portion can be connected to zonules of the eye and the central portion corresponds to a center of a pupil of the eye, and the intermediate portion of the capsule is coupled to the peripheral portion. The lens may comprise a natural lens of the eye, and the portion of the lens capsule may comprise an anterior capsule having an anterior outer surface. The support can be adhered to the anterior outer surface of the intermediate portion to increase accommodation of the central portion.

In many embodiments, the support is placed at least partially between the anterior capsule and the iris, the support comprising a thickness dimensioned such that the iris slides over the support when the iris contracts and dilates, and the support comprises a light absorbing material such that the support appears dark and appears as the pupil when the iris slides over the support.

In many embodiments, the support may comprise at least one curved surface corresponding to curvature of the lens and wherein the support comprises a thickness of no more than about 500 um.

In many embodiments, the support comprises at least one flat surface.

In many embodiments, the central portion of the lens capsule protrudes anteriorly from the support with an elevation of the central portion so as to increase a curvature of the anterior lens capsule when the eye accommodates. The central portion of the lens capsule may protrude from the support with the elevation an amount greater than without the support, and the curvature of the central portion may comprise an amount greater than the eye without the support.

In many embodiments, the support comprises a substantially annular structure extending around the central portion so as to enclose the central portion and define an outer boundary of the central portion with the support, and the central portion comprises a protrusion extending anteriorly when the eye accommodates.

In many embodiments, the support comprises an annular oval shape profile and wherein the intermediate portion comprises an annular oval portion coupled to the annular oval support to correct an astigmatism of the eye. The central portion may comprise a tonic shape profile when the eye accommodates to correct the astigmatism of the eye.

In many embodiments, the intermediate portion comprises a tonic shape profile.

In many embodiments, the support extends substantially around the central portion so as to enclose the central portion and define an oval outer boundary of the central portion. The central portion protrudes anteriorly from the oval outer boundary with an elevation and comprises a toric shape profile to correct the astigmatism when the eye accommodates.

In many embodiments, the support extends substantially around the central portion so as to enclose the central portion and define an oval outer boundary of the central portion and wherein the central portion protrudes anteriorly from the oval outer boundary with an elevation and comprises a toric shape profile to correct the astigmatism when the eye accommodates.

In many embodiments, the support is adhered to an anterior surface of an anterior capsule comprising the intermediate portion, and the support is used to guide removal of the central portion with a capsulorhexis to remove the central portion.

In many embodiments, the lens comprises an accommodating IOL.

In many embodiments, a central portion of the lens capsule is removed with a capsulorhexis, the removed central portion comprising a dimension across of at least about 4 mm, and the support comprises an inner dimension across of at least about 4 mm. The capsule moves the peripheral portion radially inward toward the lens with a force of at least about 3 g.

In many embodiments, the accommodating IOL has a haptic to move the IOL, and a structure of the support is aligned with the haptic to couple the structure to the haptic to increase the amount of accommodation.

In many embodiments, support comprises a plurality of elongate segments passed through an incision and adhered on the lens capsule such that the support is assembled in situ within the eye.

In many embodiments, the support comprises an annular structure having an inner diameter across and outer diameter across corresponding to a width of the annular structure, and the thickness comprises no more than about half of the width.

In many embodiments, the annular structure comprises a ring.

In many embodiments, the annular structure defines an aperture having a center, and the center is aligned with a pupil corresponding to a visual axis of the eye.

In many embodiments, the support is adhered to the intermediate portion of the capsule and comprises a modulus of at least about 600 kPa, such that the support moves the peripheral portion inward radially when the eye accommodates. The support may comprise one or more of metal, nickel, titanium, nitinol, silicone, plastic, polypropylene, acrylate, ceramic or polycarbonate.

In many embodiments, the support is adhered with an adhesive, the adhesive comprising one or more of cyanoacrylate, temperature sensitive adhesive, thermoreversible adhesive, a curable adhesive, a patterned microstructure based adhesive, a glycoprotein based adhesive or a crosslinker such as a photosensitive crosslinker.

In many embodiments, the support is adhered to the intermediate portion with mechanical coupling comprising one or more of clamping, locking, threads, bayonet mounting or mechanical force.

In many embodiments, the support is adhered to the intermediate portion with tack welding.

In many embodiments, the support comprises an adjustable support. A dimension across the support can be adjusted to adjust one or more of a refraction of the eye for far vision or an amount of accommodation of the eye. The dimension across the support can be increased to decrease myopia of the eye or increased to decrease hyperopia of the eye.

In many embodiments, the support comprises a shape changing material, and the shape changing material is treated with energy to adjust a dimension across the support. The shape changing material may comprise a heat sensitive material, and the support can be heated with light energy to stiffen the support when the support is coupled to the intermediate portion.

In many embodiments, the shape changing material comprises one or more of a metal or a polymer.

In many embodiments, the adjustable support comprises layers of polymer and wherein the layers of polymer are arranged in a progressively stiffer membrane such that inner layers comprise more stiffness than outer layers, and at least one inner layer is severed so as to release an amount of contractual force increase the dimension across the support.

In many embodiments, the at least one layer is severed with one or more of laser energy, laser pulses, Nd:YAG laser pulses, femto second laser pulses or mechanical cutting.

In many embodiments, the support is treated with light energy to weaken the support when the support is coupled to the intermediate portion.

In many embodiments, the support comprises an oval support, and a long dimension of the oval is aligned with an axis of an astigmatism of the eye to correct the astigmatism of the eye.

In many embodiments, spherical aberration of the eye is decreased with the support placed on the intermediate portion.

In many embodiments, the support comprises a structure having protrusions separated by a distance dimensioned to receive the portion of the lens capsule.

In many embodiments, the structure comprises a channel, and the protrusions comprise rims extending circumferentially around the support, each rim having an inner surface to contact the portion of the capsule, the distance extending between the inner surfaces of the rims.

In many embodiments, the intermediate portion of the capsule is introduced between the protrusions to couple the intermediate portion to the support.

In many embodiments, an adhesive is positioned on the intermediate portion in an annular pattern, and the adhesive is hardened on the intermediate portion of the capsule such that the support comprises hardened adhesive, and the glue sticks to the intermediate portion when hardened to couple the support to the peripheral portion.

In many embodiments, the support comprises a first elongate narrow profile through an insertion in a cornea of the eye of no more than about 2 mm, and the support is expanded to a wide profile configuration and coupled to the intermediate portion of the lens capsule when the support comprises the expanded wide profile configuration.

In another aspect embodiments provide an apparatus to treat an eye having a lens, the lens having a capsule. An expandable support comprises a first narrow profile configuration and a second wide profile configuration, the narrow profile configuration sized to pass through an incision, the wide profile configuration sized to extend substantially along an intermediate portion of the lens capsule to decrease radial movement of the intermediate portion and increase an amount of accommodation of the eye.

In many embodiments, the support in the expanded configuration comprises an arcuate profile extending along the intermediate portion so as to define an opening sized to pass light through a pupil of the eye, and the support comprises a modulus of at least about 600 kPA such that the support decreases the radial movement of the intermediate portion when the eye accommodates.

In many embodiments, the support comprises a thickness dimensioned such that the iris slides over the support when the iris contracts and dilates, and the support comprises a light absorbing material such that the support appears dark when the iris slides over the support.

In many embodiments, the apparatus further comprising a biocompatible adhesive to adhere the support to the intermediate portion of the lens capsule. The adhesive may comprise one or more of adhesive comprising one or more of cyanoacrylate, temperature sensitive adhesive, thermoreversible adhesive, a curable adhesive, a patterned microstructure based adhesive, a glycoprotein based adhesive or a cross-linker such as a photosensitive crosslinker.

In many embodiments, the support comprises an adjustable support in the second expanded configuration such that a dimension across the support is adjustable to adjust one or more of a refraction of the eye for far vision or an amount of accommodation of the eye.

In many embodiments, the support comprises a shape changing material to adjust the dimension across the support when the support is treated with energy.

In many embodiments, the shape changing material comprises a heat sensitive material to stiffen the support when the support is coupled to the intermediate portion.

In many embodiments, the shape changing material comprises one or more of a metal or a polymer.

In many embodiments, the adjustable support comprises layers of polymer, and the layers of polymer are arranged in a progressively stiffer membrane such that inner layers comprise more stiffness than outer layers, and at least one inner layer is severed so as to release an amount of contractual force increase the dimension across the support.

In many embodiments, the support comprises an oval support in the second expanded profile configuration to align a long dimension of the oval with an axis of an astigmatism of the eye to correct the astigmatism of the eye.

In many embodiments, the oval support comprises an annular oval shape profile having an inner boundary sized to extend substantially around the central portion and define the central portion with an oval outer boundary.

In many embodiments, the support comprises a structure having protrusions separated by a distance dimensioned to receive the portion of the lens capsule. The structure may comprise a channel, and the protrusions comprise rims extending circumferentially around the support, each rim having an inner surface to contact the portion of the capsule, the distance extending between the inner surfaces of the rims.

In many embodiments, the expandable support comprises a plurality of elongate segments sized to pass through the incision to form the support in situ. The plurality of elongate segments comprises a first plurality of elongate segments to couple to an anterior lens capsule and a second plurality of elongate segments to couple to a posterior lens capsule.

In many embodiments, the support comprises a first portion having a first structure to couple to a first haptic and a second portion having a second structure to couple to a second haptic so as to focus force to the first haptic and the second haptic when the first portion is aligned with the first haptic and the second portion is aligned with the second haptic.

In many embodiments, the support is configured to decrease spherical aberration of the eye.

BRIEF DESCRIPTION OF THE DRAWINGS

FIG. 2A-1 shows protrusion and increased curvature of the anterior lens capsule when the eye accommodates with intermediate portion of the lens capsule stiffened to increase accommodation, in accordance with embodiments of the present invention;

FIG. 2A-2 shows the elevation, diameter and increased optical power of the protrusion as in FIG. 2A-1 when the eye accommodates;

FIG. 2A-3 shows the optical power of the central portion of the lens corresponding to the protrusion of the central portion of the lens capsule when the eye accommodates, in accordance with embodiments of the present invention;

FIG. 2B shows an eye having an intermediate portion of the anterior lens capsule and an intermediate portion of the posterior lens capsule stiffened to increase accommodation, in accordance with embodiments of the present invention;

FIG. 2M1 shows a narrow profile configuration for insertion into the eye through the incision with rotation of the support shown in 2L;

FIG. 3A1 shows the support as in FIG. 3A suitable for use with an accommodative IOL, in accordance with embodiments of the present invention;

FIGS. 3E1 and 3E2 show a first plurality of the curved elongate segments aligned on the anterior lens capsule and a second plurality of the curved elongate segments aligned on the posterior lens capsule, respectively, so as to vault the lens capsule and increase accommodation, in accordance with embodiments of the present invention;

DETAILED DESCRIPTION OF THE INVENTION

Embodiments of the present invention as described herein can be used in many ways to improve accommodation of the eye. The embodiments as described herein can be used to treat presbyopia with an otherwise healthy eye, in a non-invasive or minimally invasive manner, such that the accommodation of the natural lens of the eye is enhanced. The embodiments as described herein can also be used in conjunction with IOLs such that the amount of accommodation with the IOL can be increased. The accommodating IOL may comprise a deformable IOL that can provide increased curvature when the eye accommodates, or an IOL in which the support increases an amount of axial movement of the lens when the eye accommodates, or combinations thereof.

The treatment of the capsular tissue can increase radially inward force to an IOL from at least about 1 gram (hereinafter "g") to at least about 3 g, for example at least about 4 g, in exemplary embodiments at least about 6 g, so as to provide corresponding improvement in accommodation, for example at least about a two fold increase, for example about a three fold increase, in the amount of accommodation when combined with a commercially available accommodating IOL.

The embodiments as described herein can be used in combination with other treatments such as a phakic IOLs, intracorneal inlays, laser softening of the lens, IOLs, for example accommodating IOLs so as to increase substantially the amount accommodation of the implanted accommodating IOLs.

Alternatively or in combination with increasing an amount of accommodation of the eye, the stiffening support as described herein can be used to treat astigmatism of the eye, and may decrease spherical aberration of the eye, for example with increased accommodation of the eye.

Figure 1A:
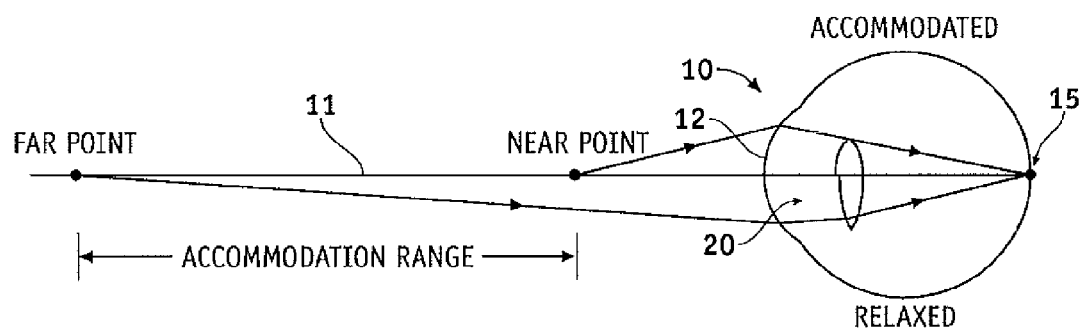
FIG. 1A shows accommodation of an eye, suitable for incorporation in accordance with embodiments of the present invention.

FIG. 1A shows accommodation of an eye 10. The eye 10 has a cornea 12 and a lens 20. The cornea and lens focus light on a retina 15 such that the patient perceives the image with the light sensitive tissue of the retina. When the image on the retina is focused, the image appears sharp to the patient. However, when the image is out of focus, the image appears blurred. The lens 20 of the eye accommodates to the distance of the object viewed such that the image of the object is focused on the retina and remains sharp to the patient. For far vision, the lens 20 of eye 10 relaxes to focus on a far point. The far point can be several meters away, such that the vergence of the target is approximately 0 Diopters. The near point can be located at a distance suitable for reading, for example, and can be about 12 inches (⅓ meter) from the eye, for example, such that the vergence of the object is about 3 Diopters. The accommodation range corresponds to the range over which the eye can accommodate so as to bring the viewed object into focus. The amount of accommodation can be expressed with the optical power used to bring an object into focus, and the optical power can be expressed in units of Diopters (hereinafter "D"), to bring the object into focus. For an emmetropic eye capable of focusing on an object at a far distance of about 10 meters and an object at a near distance of about ⅓ of a meter from the patient, the amount of accommodation expressed as a range of optical power is at least about 3 D.

Figure 1B:
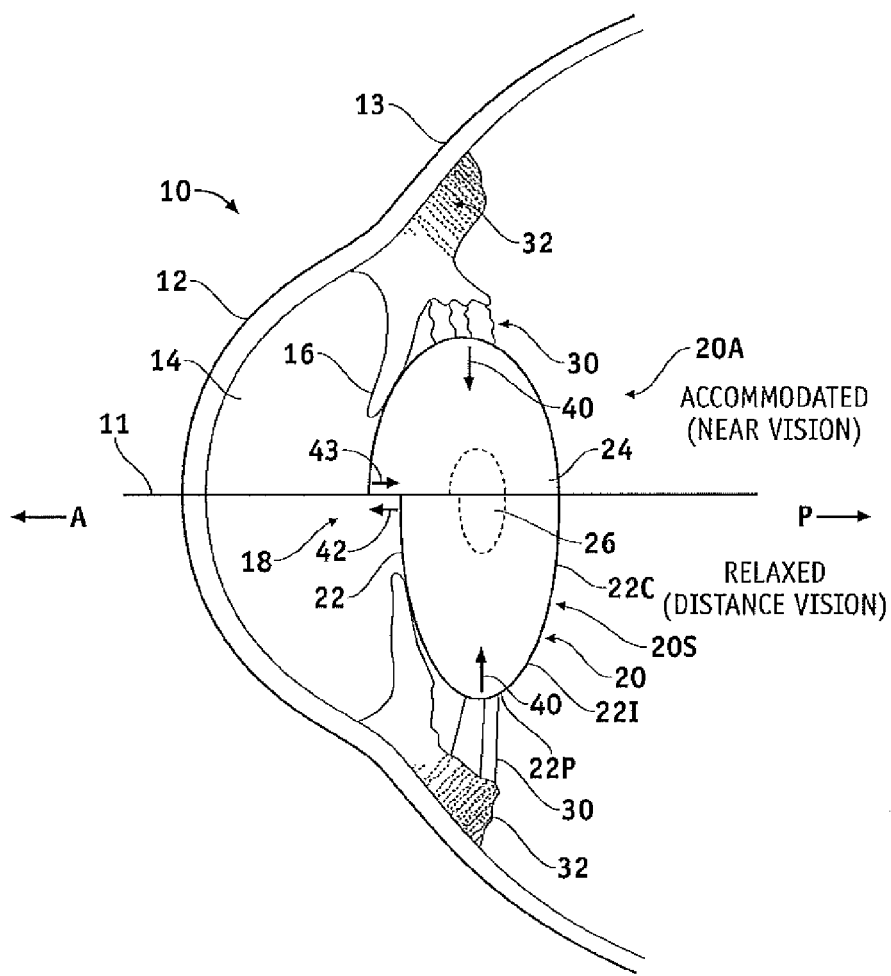
FIG. 1B shows structures of the eye as in FIG. 1A.

FIG. 1B shows structures of the eye as in FIG. 1A. The eye 10 comprises cornea 12, an anterior chamber 14 and an iris 16. The cornea 12 has about two thirds of the optical power of the eye, and is optically coupled to the lens 20 so as to focus light on the retina of the eye. The eye 10 has a sclera 13 comprising the visible white portion of the eye. The iris 16 can define a pupil 18 of the eye. The eye may comprise an axis 11. The axis 11 may correspond to one or more known axes of the eye such as the visual axis of the eye and the optical axis of the eye. The iris 16 may contract slightly when the eye accommodates. The lens 20 comprises a capsule 22, a cortex 24 and a nucleus 26. The eye has ciliary muscles 32 connected to ciliary zonules 30. The ciliary zonules 30 are connected to lens capsule 22 at a peripheral portion 22P of the lens capsule.

Description of the eye 10 suitable for combination in accordance with the embodiments as described herein with reference to FIG. 1A and FIG. 1B is at least partially described in one or more the following publications by Adrian Glasser:

Glasser, A. (2010) Accommodation. In: Darlene A. Dartt, editor. Encyclopedia of Eye, Vol I. Oxford: Academic Press; p. 8-17.

Glasser, A. (2004) Physiology of Accommodation and Presbyopia, In *Surgery for Hyperopia*. Ed. Neil Sher, pp. 11-21, SLACK, Inc. Thorofare, N.J.

Glasser, A. (2003) The Helmholtz Mechanism of Accommodation. In *Current Research in Eye Surgery Technology (CREST)*. Eds. K. Tsubota, B. S. Boxer Wachler, D. T. Azar, D. Koch. pp. 27-47. Marcel Dekker, Inc., New York.

Glasser, A. and Kaufman, P. L. (2002) Accommodation and Presbyopia. In *Adler's Physiology of the Eye*. 10th Edition. Eds Kaufman P. L. and Alm, A. pp. 195-233. Mosby, SI. Louis.

During accommodation, the lens and ciliary components of the eye adjust to bring an object into focus. When the eye has a "relaxed" configuration for far vision, the ciliary muscle 32 of the eye is relaxed such that zonules 30 pull the lens capsule 22 outward. When the eye accommodates for near vision, the ciliary muscle 32 contracts such that zonules 30 allow the lens peripheral portion 22P of the lens capsule to move radially inward with a radially inward force 40. When the peripheral portion 22P moves radially inward, the front portion of the lens capsule moves forward with anterior movement 42 such that the anterior optical surface of the lens moves forward so as to bring the image of the near object into focus on the retina. In addition, the curvature of the anterior surface of the lens 20 can increase when the front portion of the lens capsule moves forward so as to increase the optical power of the lens 20 and bring the image of the object into focus on the retina. When the peripheral portion 22P moves radially outward, the front portion of the lens capsule moves with posterior movement 43 such that the anterior optical surface of the lens moves posteriorly and decreases curvature so as to bring the image of the far object into focus on the retina.

With presbyopia, the inner components of the lens such as the cortex 24 may stiffen, such that the amount of accommodation decreases. The amount of anterior movement 42 of lens 22 and the amount corresponding curvature change decrease such that the eye is no longer capable of bringing both near and far objects into focus with accommodation.

Figure 1C:
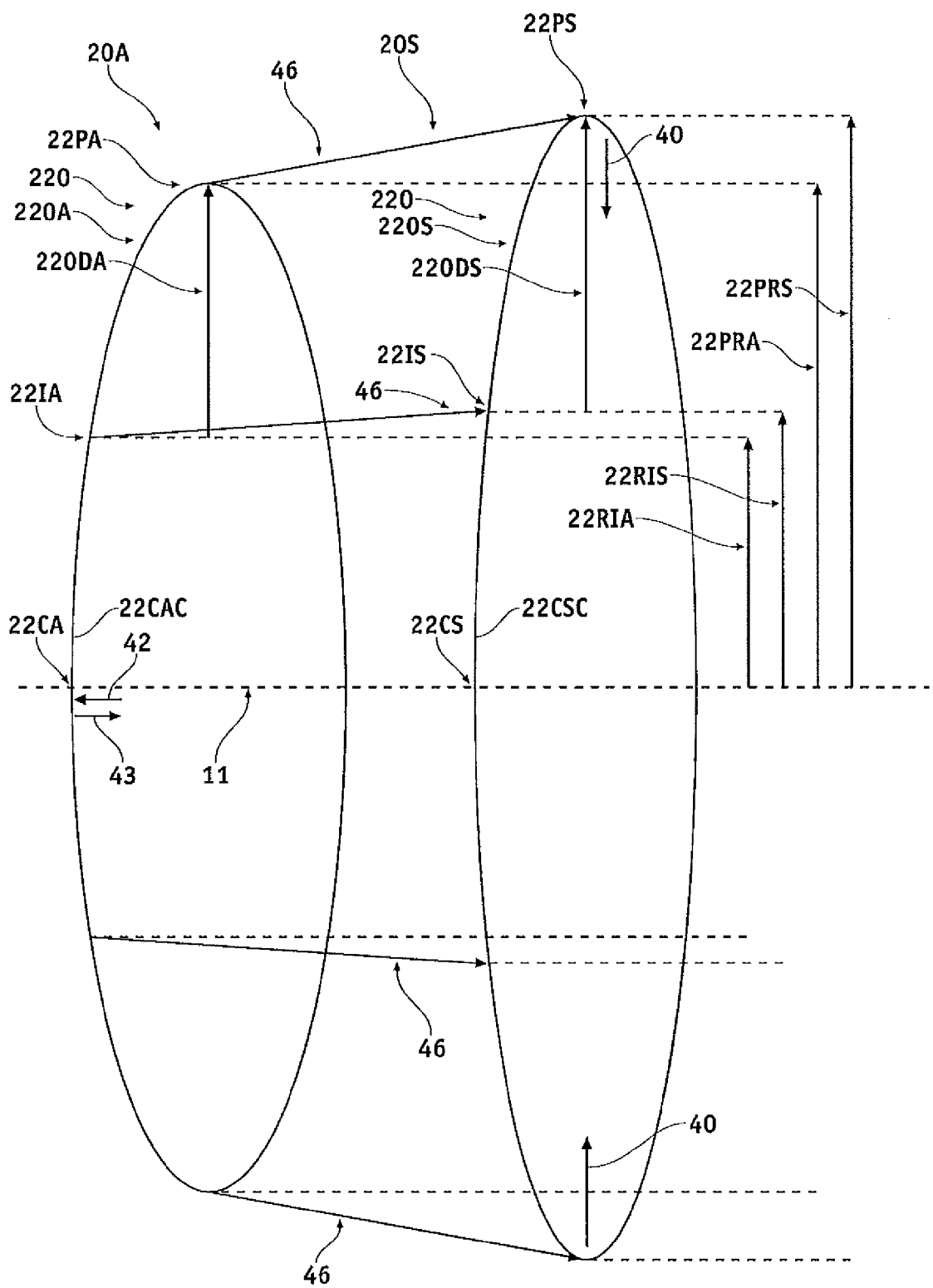
FIG. 1C shows elastic stretching of the lens capsule of the eye as in FIGS. 1A and 1B, suitable for incorporation in accordance with embodiments as described herein.

FIG. 1C shows elastic stretching of the lens capsule 22 of the eye as in FIGS. 1A and 1B, suitable for incorporation in accordance with embodiments. The lens of the eye comprises a first relaxed configuration 20A of the lens capsule for accommodation, and a second stretched configuration 20S of the lens capsule for far vision. The first relaxed configuration 20A corresponds to constriction of the ciliary muscle 32 such that tension on zonules 30 is decreased such that and the lens can relax and move forward with anterior movement 42. The second stretched configuration 20S corresponds to radially outward stretching of the lens when the ciliary muscles of the eye relax and the zonules attached to the peripheral portion 20P stretch the lens capsule and move the lens radially outward, such that and the lens can stretch and move with posterior movement 43. The correspondence of locations of lens 20 for the relaxed lens configuration 20A for accommodation and the stretched lens configuration 20S are shown with arrows 46.

The lens 20 stretches when the ciliary muscles relax such that the capsule is stretched radially outward. The relaxed lens configuration 20A for accommodation for near vision has a central portion 22C of the lens capsule 22, an intermediate portion 22IA, and a peripheral portion 22AP. The relaxed configuration 20A for accommodation comprises the central portion 22CA located along axis 11, the intermediate portion 22IA located a radial distance 22RIA from axis 11 and the peripheral portion 22PA located a radial distance 22PRA from axis 11. The relaxed configuration 20A comprises an outer portion 22OA extending from the intermediate portion 22IA to the peripheral portion 22PA with a distance 22ODA. The central portion 22CA has a curvature 22CAC when the lens comprises the relaxed configuration for accommodation.

The stretched lens configuration 20S for far vision has a central portion 22CS of the lens capsule 22, an intermediate portion 22IS, and a peripheral portion 22AS. The stretched lens configuration 20S for far vision comprises the central portion 22CS located along axis 11, the intermediate portion 22IS located a radial distance 22RIS from axis 11 and the peripheral portion 22PS located a radial distance 22PRS from axis 11. The stretched configuration 20S comprises an outer portion 22OS extending from the intermediate portion 22IS to the peripheral portion 22PS with a distance 22ODS. The central portion 22CS has a curvature 22CSC when the lens comprises the stretched configuration for far vision.

The stretching of lens capsule 22 with lens configuration 20S can store energy and provide an increased amount of radially inward force 40, so as move the anterior capsule forward with anterior movement 42. The stretching of lens capsule 42 extends from axis 11 to peripheral portion 22P.

The radial distance 22PRS is greater than the radial distance 22PRA, corresponding to stretching of the central portion 22C, the intermediate portion 22I, the outer portion, and the peripheral portion 22P. The radial distance 22RIS is greater than the radial distance 22RIA corresponding to stretching of the intermediate portion 22I and central portion 22C. The radial distance 22ODA is less than the radial distance 22ODS corresponding to stretching of the outer portion 22O located between intermediate portion 22I and peripheral portion 22P. Although the stretched components of the lens capsule can move the peripheral portion 22P radially inward with the force 40, the presbyopic lens can be stiffer than the non-presbyopic lens such that the anterior movement 42 and the corresponding curvature change may not be enough to provide accommodation.

Figure 2A:
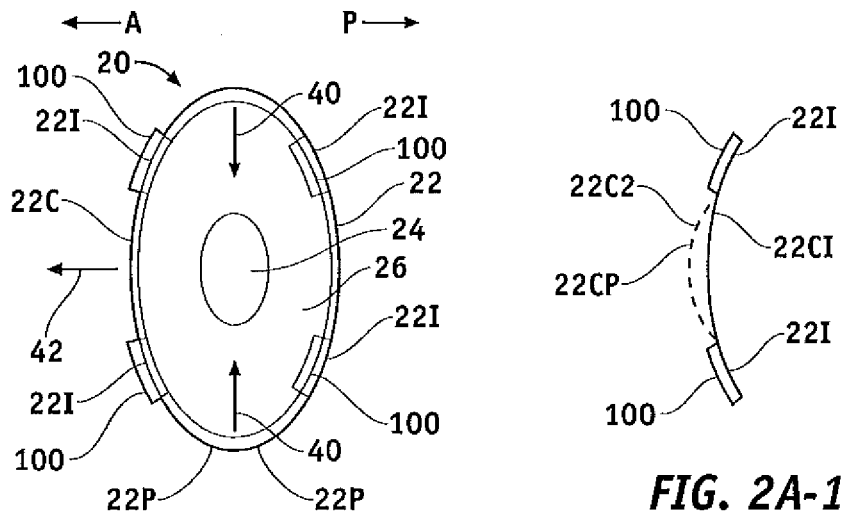
FIG. 2A shows a side view an eye having an intermediate portion of the anterior lens capsule stiffened to increase accommodation, in accordance with embodiments of the present invention.
Figure 2A:
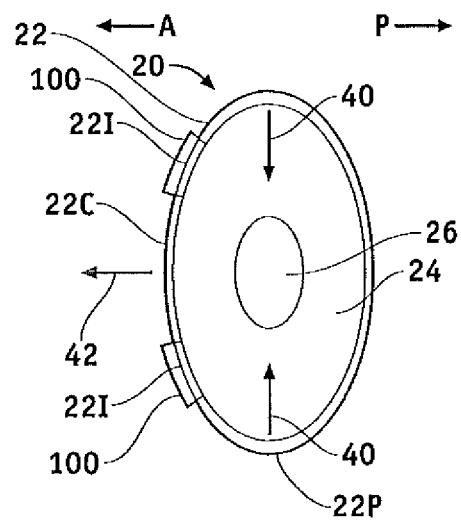

FIG. 2A shows a side view eye 10 having an intermediate portion 22I of the anterior lens capsule coupled to a support 100 to stiffen the intermediate portion to increase accommodation. This stiffening of the anterior capsule can be less invasive than stiffening the posterior capsule, for example, and can be used in many embodiments that comprise increasing the amount of accommodation of natural lens of the eye, for example. The intermediate portion 22I is disposed between an inner central optical portion 22C and a peripheral portion 22P attached to the zonules. The eye comprises an anterior orientation A toward the cornea and a posterior orientation P toward the retina.

The inner central optical portion 22C comprises an optically useful portion of the lens capsule 22, and corresponds to light transmitted through the pupil of the eye. The intermediate portion 22I can be located away from the central portion 22C such that the central portion remains optically clear and substantially free from aberrations and light scatter. The intermediate portion may correspond to a portion of the capsule covered by the pupil, for example in bright light. In many embodiments, the intermediate portion is covered by the pupil in dim illumination, for example, such that the patient can receive the benefit of increased accommodation when reading in dim light or viewing objects in dim light for example. The intermediate portion may comprise an intermediate portion of the anterior capsule, or an intermediate portion of the posterior capsule, or both, for example.

The stiffened intermediate portion of the capsule 22I can increase accommodation of the eye 10 in many ways. The accommodation can be increased with one or more of increased radially inward force 40 of the lens capsule, increase anterior movement 42 of the lens capsule, increased curvature 22AC of the lens capsule, or increased curvature 22CPC of the central portion comprising a protrusion 22CP (FIG. 2A-2), or combinations thereof. With the stiffened portion 22I, the radially inward force 40 can be increased when the ciliary muscles of the eye contract and the zonules allow the peripheral portion of the capsule to move inward. The increased radially inward force 40 can provide an increased amount of the anterior movement 42 of the lens capsule. The increased anterior movement 42 of the lens may provide an increased curvature 22CAC of the central portion 22CA when the lens accommodates so as to increase accommodation of the eye. Also, the increased anterior movement 42 of the lens capsule may provide increased accommodation based at least partially on an increased distance from the central portion 22C of the lens capsule to the retina. Alternatively or in combination, the increased forward axial movement 42 may provide protrusion 22CP having increased curvature 22CPC when the eye accommodates as described herein with reference to FIG. 2A-2, for example.

The stiffening support as described herein can increase the modulus, for example the Young's modulus of the lens capsule of the intermediate portion 22I. The lens capsule may comprise a Young's modulus within a range from about 1.5 mN/mm2 to about 3 mN/mm2, for example. (See Weeber H A., Martin H. The Role of the Capsular Bag in Accommodation. In: Guthoff R, Ludwig K, eds. Current Aspects of Human Accommodation II. Heidelberg: Kaden Verlag; 2003). Although the material properties of the lens capsule can be at least somewhat non-linear and the Young's modulus of the lens capsule can vary with age, a person of ordinary skill in the art can determine empirically the thickness and corresponding modulus based on the teachings described herein, so as to provide stiffening treatment to the intermediate portion 22I and increased accommodation.

The support can be coupled to the lens capsule in many ways. For example the support can be adhered to the lens capsule with an adhesive comprising one or more of a curable adhesive, cyanoacrylate, temperature sensitive adhesive such as Poly(N-isopropylacrylamide) (hereinafter "p-Nipam"), a patterned microstructure based adhesive such as a setae based adhesive, thermoreversible adhesive, a glycoprotein based adhesive such as a glycosylated hudroxytryptophan, or a cross-linker such as a photosensitive crosslinker. The setae may comprise setae similar to gecko footpads having the attractive forces that hold the setae to surfaces with van der Waals interactions between the finely divided setae and the surface of the lens capsule. The support can be coupled to the capsule mechanically, for example with sutures, tabs or channels, and can be tack welded to the capsule.

Figures 2, 2A:
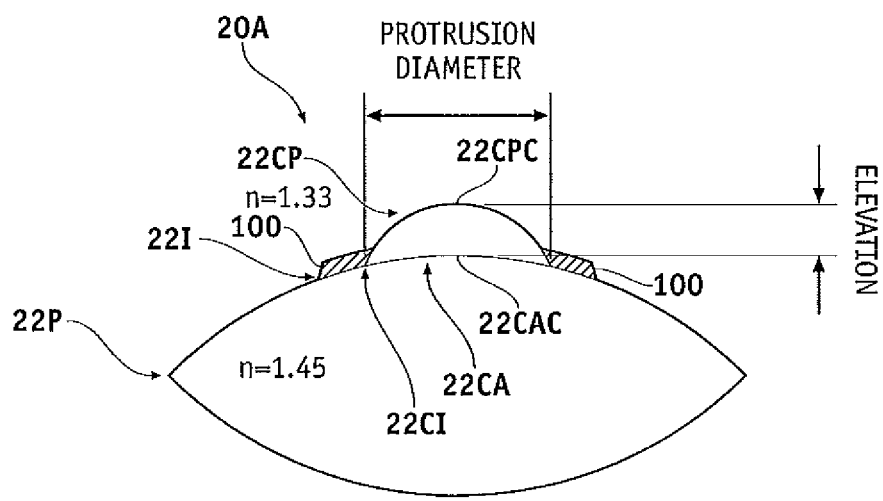
Figures 2, 2A, 3:
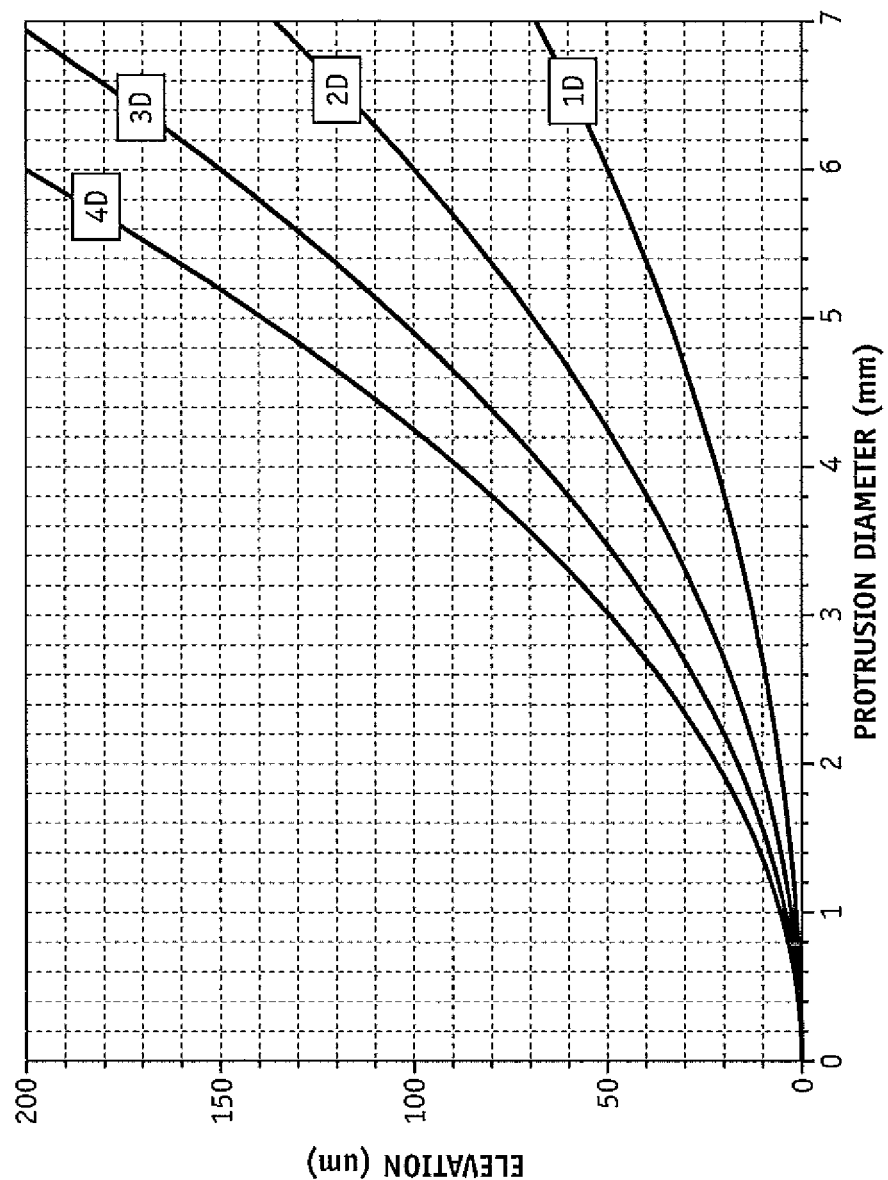
Figure 2C:
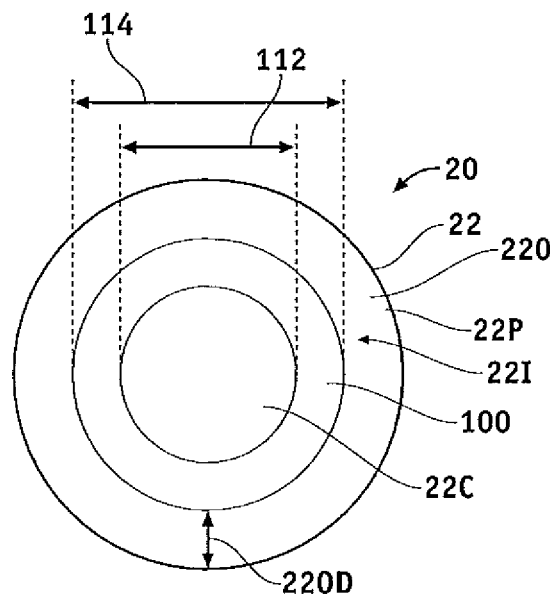
FIG. 2C shows a front view the eye having an intermediate portion of the anterior lens capsule stiffened with the support to increase accommodation as in FIG. 2A.
Figure 2E:
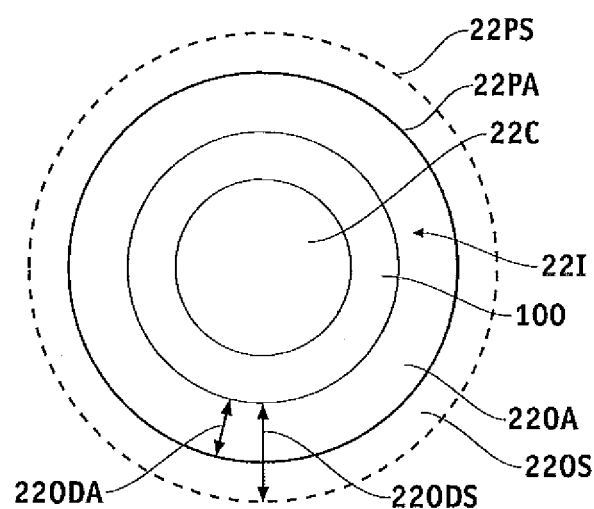
FIGS. 2D and 2E show side and front views, respectively, of the eye having the support coupled to the intermediate portion of the eye to increase elastic stretching of the lens capsule to the decrease presbyopia as in FIGS. 2B and 2C.
Figure 2D:
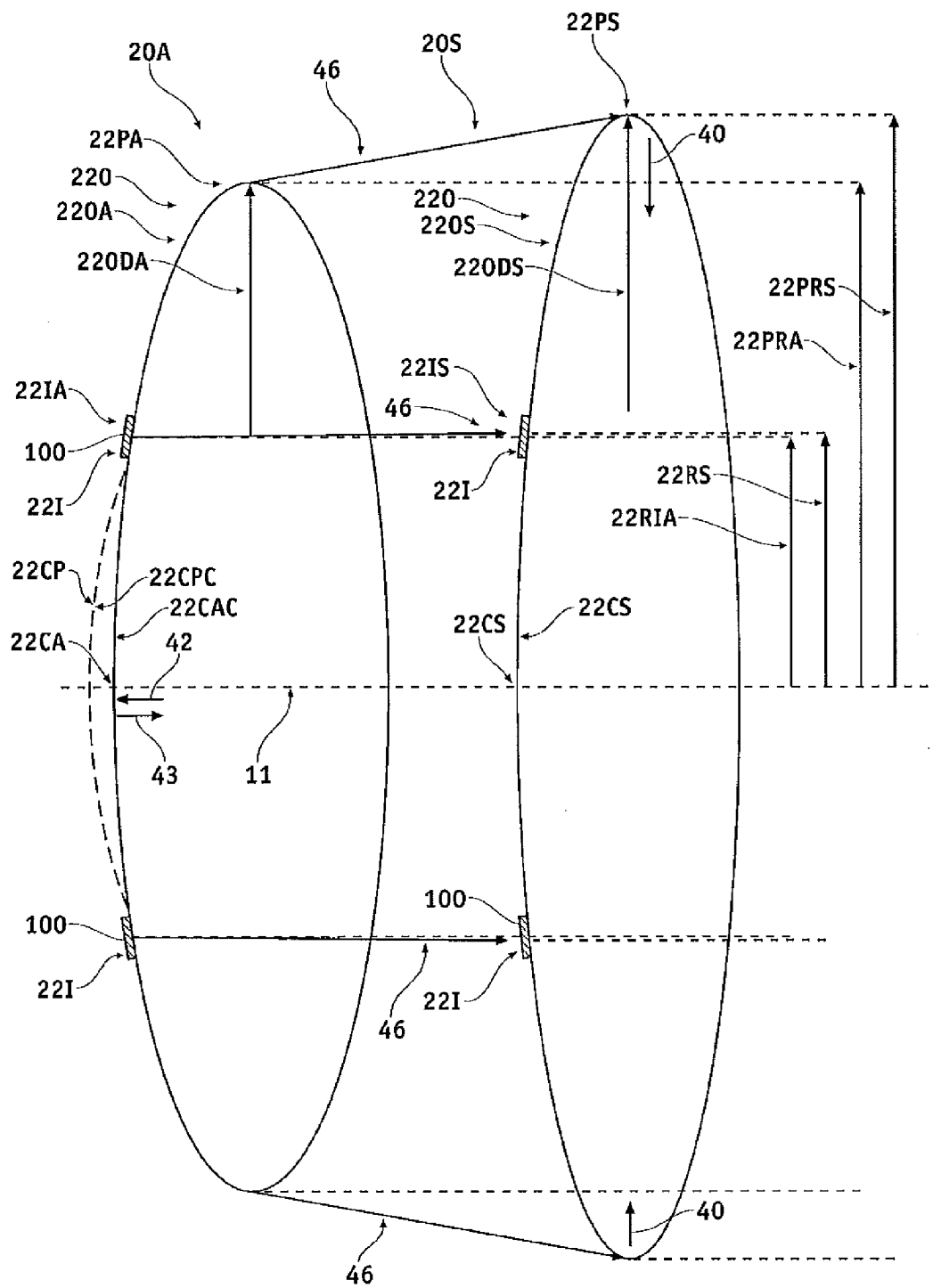
Figure 2F:
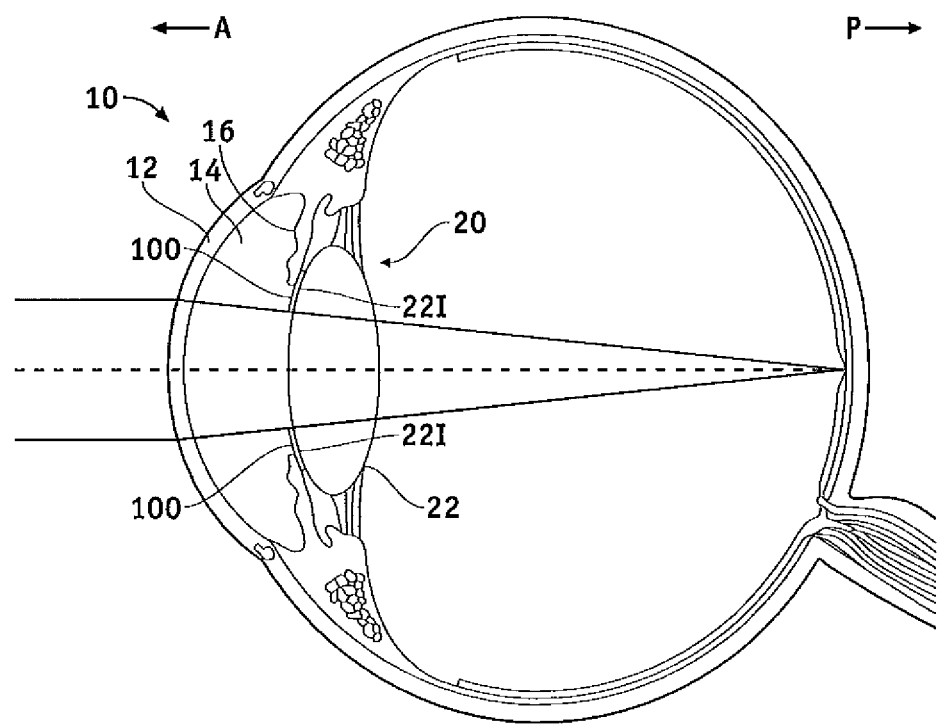
FIGS. 2F and 2G show the support coupled to the anterior lens capsule having a light absorbing material such that the support appears as the pupil when the iris slides over the support during constriction and dilation of the pupil, in accordance with embodiments.
Figure 2G:
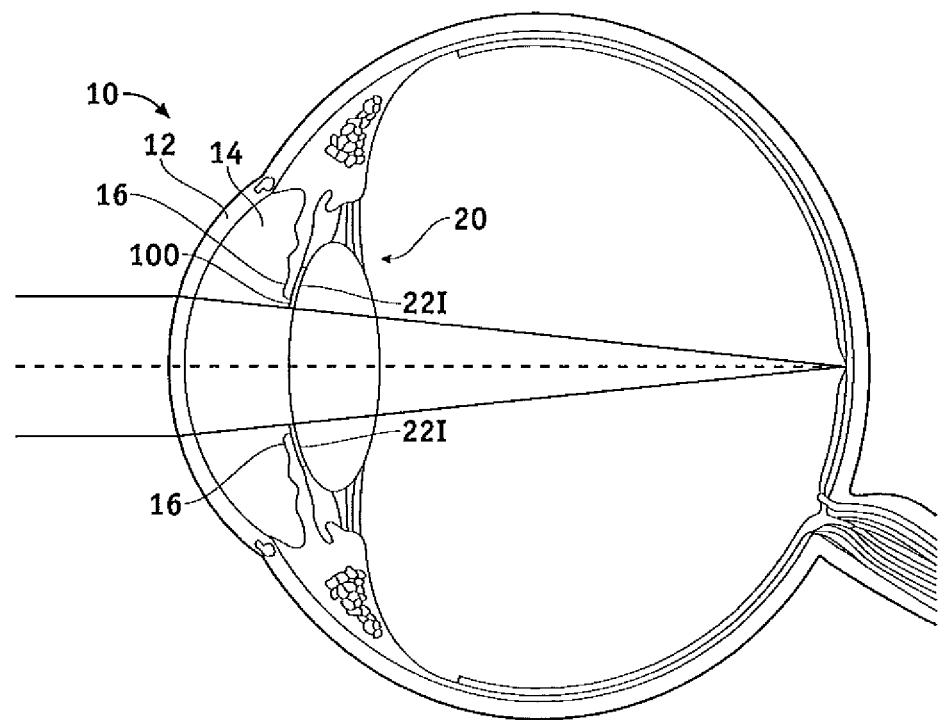
Figure 2H:
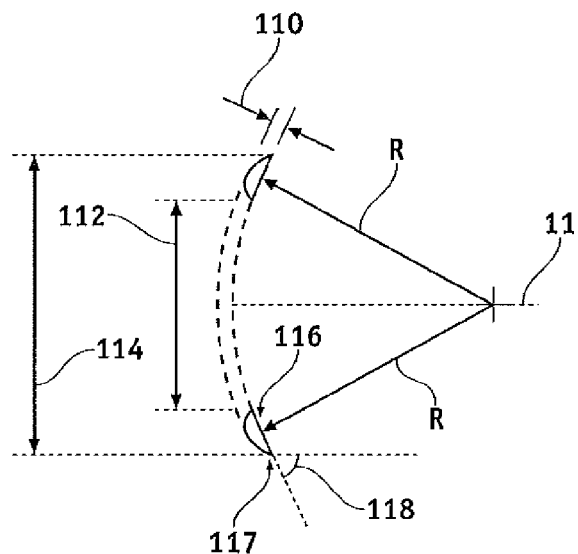
FIG. 2H shows the support comprising an inclined surface corresponding to a radius of curvature of the lens capsule to couple to the lens capsule, in accordance with embodiments.
Figure 2I:
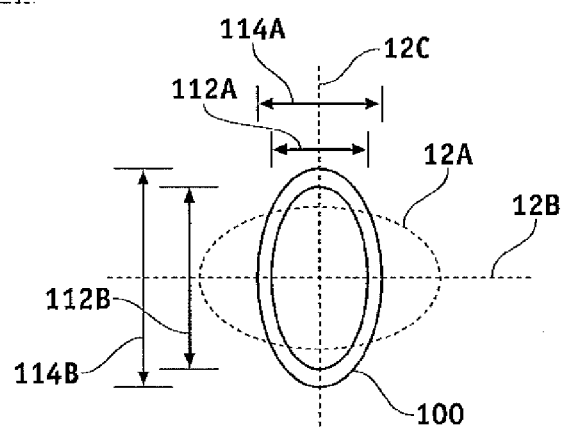
FIG. 2I shows the support comprising an oval shape to correct astigmatism of the eye, in accordance with embodiments.
Figure 2J:
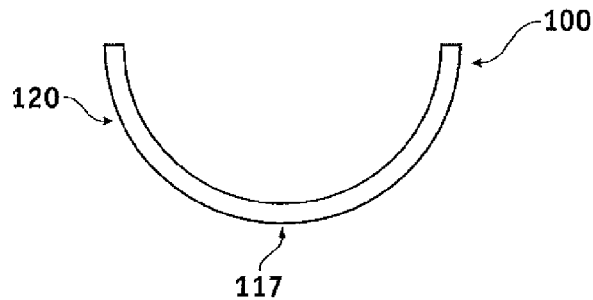
FIGS. 2J and 2K show side and end views, respectively, of the support comprising a narrow profile configuration for insertion into the eye through an incision in the cornea, in accordance with embodiments.
Figure 2K:
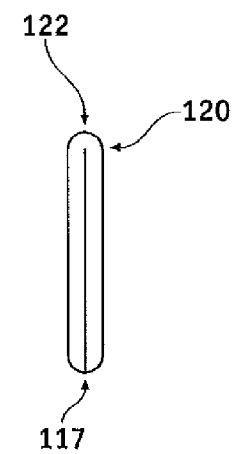
Figure 2L:
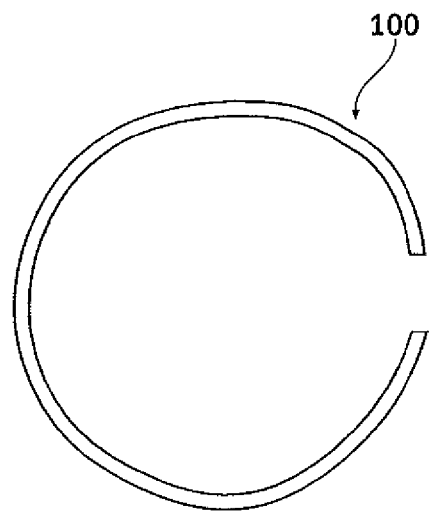
FIGS. 2L and 2M show the support comprising an expanded wide profile configuration, and narrow profile configuration for insertion into the eye through an incision in the cornea, respectively.
Figure 2M:
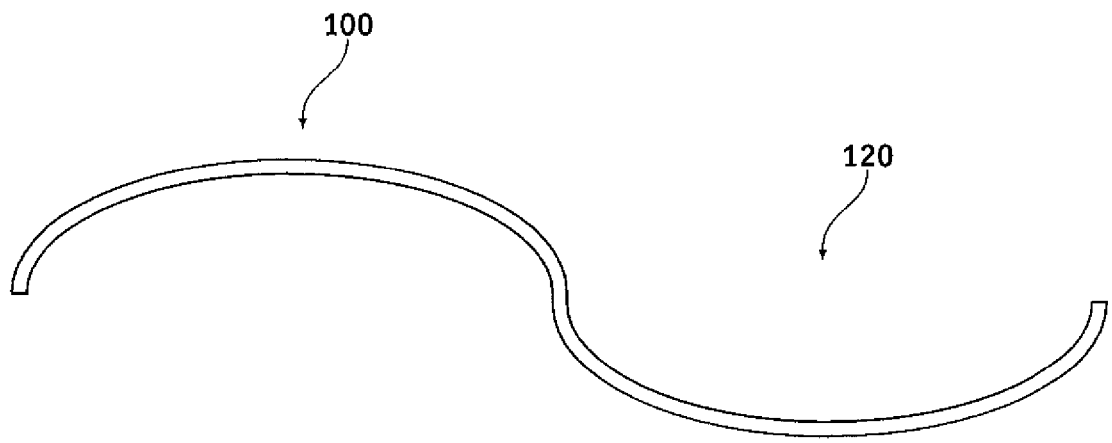
Figures 1, 2M:

FIG. 2A-1 shows increased curvature of the anterior lens capsule when the eye accommodates with intermediate portion of the lens capsule stiffened with support 100 so as to increase accommodation. The central portion of the lens capsule may comprise a first curvature profile 22C1 when the eye does not accommodate, for example when the lens capsule is stretched as described herein. The second curvature profile 22C2 may correspond to the elevation profile of a protrusion 22CP of the central portion when the eye accommodates with the intermediate portion stiffened with support 100, for example when the peripheral and outer portions of the lens capsule are not stretched and the eye accommodates. When the eye having the intermediate portion stiffened accommodates with radially inward movement of the peripheral portion 22P, the stiffened intermediate portion 22I can direct the curvature change to the non-stiffened central portion 22C, such that the central portion 22P moves anteriorly a greater amount than intermediate portion 22I. The central portion having protrusion 22CP has the increased change in curvature corresponding to increased optical power of the central portion 22C. The elevation profile of protrusion 22CP can be measured relative to the outer boundary of central portion 22C defined by the inner dimension of annular support 100.

FIG. 2A-2 shows the diameter, elevation and increased optical power corresponding to the curvature 22CPC of the protrusion 22CB when the eye accommodates with the intermediate portion 22I of the lens capsule stiffened with support 100. The lens 20 has a configuration 20A for accommodation with the outward tension of the zonules decreased such that lens capsule relaxes and the peripheral portion 22P has moved radially inward. The protrusion 22CP of the central portion 22C has an elevation relative to a reference surface profile comprising the surface of the central portion 22CA when the eye accommodates naturally as described above without the stiffening treatment of the intermediate portion 201. The elevation of the central portion 22C comprising protrusion 22CP may comprise an inflection 22C1 extending around the protrusion 22CP where the curvature of the lens capsule may change abruptly and the stiffened intermediate portion 22I couples the central portion 22C. Alternatively to the abrupt change in curvature, the curvature near inflection 22C1 can increase gradually with a graded transition profile such that the central portion 22C comprises a prolate elevation profile so as to correct spherical aberration of the eye.

The increased elevation and curvature of the central portion relative to the peripheral portion can increase the optical power of the central portion substantially. The lens has an index of refraction of about 1.45 and the aqueous humor has an index of refraction of about 1.33, such that the curvature of the central portion 22C provides optical power. The optical power of the protrusion can be determined based on the curvature corresponding to the height and diameter of the protrusion 22CP.

FIG. 2A-3 shows the increased optical power corresponding to curvature 22CPC for varying diameters and elevations of the protrusion 22CP when the eye accommodates. The elevation of the protrusion is proportional to the optical power in Diopters (D) and to the square of the protrusion dimension across, for example a diameter across for a spherical protrusion. The diameters and corresponding elevations so as to provide curvature changes corresponding 1 D, D, 3 D and 4 D of accommodation are shown in Table I. For a curvature corresponding to the 1 D protrusion having a diameter of 5 mm, the elevation is about 35 um. For a curvature corresponding to a 2 D protrusion having the 5 mm diameter, the elevation is about 70 um. A comparison of the elevation of the 1 D protrusion to the 2 D protrusion shows the approximately linear relationship of optical power to protrusion elevation. For a 1 D protrusion having a diameter of about 3 mm, the elevation is about 12 um. For the 1 D protrusion having a diameter of about 6 mm the elevation is about 50 um. A comparison of the 1 D protrusion having the diameter of 3 mm to the 1 D protrusion having the diameter of about 6 mm shows that the elevation is approximately proportional to the square of the diameter. Based on the dimensions shown, a protrusion 22CP having an exemplary 4 mm diameter and a height of about 45 um can have an increased curvature so as to provide about 2 D of additional accommodative optical power.

TABLE I

Diameters and corresponding elevations to provide curvature changes corresponding 1 D, 2 D, 3 D and 4 D of increased accommodation.

| Diameter mm | Elevation @ 1 D | Elevation @ 2 D | Elevation @ 3 D | Elevation @ 4 D |
| --- | --- | --- | --- | --- |
| 0 | 0 | 0 | 0 | 0 |
| 0.5 | 0.347 | 0.694 | 1.04 | 1.39 |
| 1 | 1.39 | 2.78 | 4.17 | 5.56 |
| 1.5 | 3.13 | 6.25 | 9.38 | 12.5 |
| 2 | 5.56 | 11.1 | 16.7 | 22.2 |
| 2.5 | 8.68 | 17.4 | 26.0 | 34.7 |
| 3 | 12.5 | 25 | 37.5 | 50 |
| 3.5 | 17.0 | 34.0 | 51.0 | 68.1 |
| 4 | 22.2 | 44.4 | 66.7 | 88.9 |
| 4.5 | 28.1 | 56.3 | 84.4 | 112.5 |
| 5 | 34.7 | 69.4 | 104.1 | 138.9 |
| 5.5 | 42.0 | 84.0 | 126.0 | 168.1 |
| 6 | 50 | 100 | 150 | 200 |
| 6.5 | 58.6 | 117.4 | 176.0 | 234.7 |
| 7 | 68.1 | 136.1 | 204.1 | 272.2 |

The additional optical power provided by protrusion 22CP can be combined with anterior movement of the central portion 22C and the intermediate portion 22I, so as to further increase the amount of accommodative optical power when protrusion 22CP increases curvature of the central portion 22C. For example, increased stretching of the peripheral and outer portions of the lens capsule can be combined with the protrusion 22CP and the anterior movement of the intermediate portion 22I and central portion 22C, so as to provide greater than about 2 D of accommodative optical power when the protrusion 22P provides about 2 D of accommodative optical power.

FIG. 2B shows the eye having the intermediate portion 22I of the anterior lens capsule having a first support 100 coupled thereon and an intermediate portion 22I of the posterior lens capsule having a second support 100 coupled thereon so as to increase accommodation. Each intermediate portion 22I of the lens capsule 20 is stiffened with the support so as to increase accommodation of the patient.

FIG. 2C shows a front view the eye having an intermediate portion 22I of the anterior lens capsule stiffened with support 100 to increase accommodation as in FIG. 2A. An outer portion of the lens capsule 22O extends between the intermediate portion 22I and the periphery 22P. The outer portion 22O can be stretched when the support 100 is coupled to the intermediate portion 22I, such that accommodation of the eye is increased. The central portion 22C may comprise a distance across corresponding to an inner distance of support 100, such as an inner annular diameter 112 of support 100. The dimensions of the inner portion correspond to dimensions of the pupil, for example within a range of about 2 mm to about 6 mm, for example within a range from about 3 mm to about 5 mm, so as to correspond to dimensions of the presbyopic pupil. The intermediate portion 22I comprises a distance across, for example an inner annular diameter and an outer annular diameter. The inner annular diameter may correspond to the size of the diameter of the central optical portion 22C. The outer annular dimension of the intermediate zone 22I may correspond to an outer distance across support 100, for example an outer annular diameter 114 of the support. The outer annular dimension may correspond to a dimension of the dilated pupil with cycloplegia, for example, such that the intermediate portion can be accessed readily during surgery, for example when the pupil is dilated during surgery. Based on the teachings described herein, a person of ordinary skill in the art can determine dimensions of the intermediate portion so as to increase accommodation and decrease presbyopia with the natural lens of the eye, for example. The anterior capsule when treated may comprise similar dimensions, for example.

While the support 100 may comprise one or more of many shapes to inhibit radial movement, in many embodiments support 100 comprises an annular structure such as an annular ring or annular oval. The annular structure can extend substantially around the central portion 22C, so as to enclose and define the central portion 22C with the support 100. The support 100 may resist radial movement and corresponding circumferential expansion and compression of the intermediate portion 22I, so as to encourage formation of protrusion 22CP when the eye accommodates.

FIGS. 2D and 2E show side and front views, respectively, of the eye having the support coupled to the intermediate portion of the eye to increase elastic stretching of the lens capsule to increase accommodation. The support can be coupled to the lens capsule such that the strain of the intermediate portion corresponds to the relaxed capsule during accommodation so as to increase stretching of the outer portion 22O of the lens capsule when the ciliary muscle relaxes and the capsule is stretched with the zonules.

The increased stretching of lens capsule 22 with lens configuration 20S coupled to support 100 can store energy and provide an increased radially inward force as indicated by arrows 40, so as move the anterior capsule forward as indicated with arrow 42. The increased stretching of lens capsule 42 corresponds to increased stretching of outer portion 22O of the capsule between the intermediate portion 22I coupled to the support and the peripheral portion 22P coupled to the zonules. The radial distance 22RIS is similar to radial distance 22RIA corresponding to no substantial increased stretching of the intermediate portion 22I and central portion 22C. The radial distance 22ODA is less than the radial distance 22ODS corresponding to stretching of the outer portion 22O located between intermediate portion 22I and peripheral portion 22P. As the peripheral portion 22P of the lens may be pulled that radial distance 22PRS corresponds substantially to the eye without the support as shown above, the radial stretching distance 22ODS can be substantially greater for the eye with the support.

The lens capsule can be coupled to the intermediate support with amounts of strain corresponding to the relaxed lens capsule during accommodation, or amounts of strain corresponding to stretching of the lens capsule when the ciliary muscle of the eye relaxes for far vision, and amounts in between. For example, with capsulorhexis, it can be helpful to couple the support to capsule to provide support around the edge of the incision. With the natural crystalline lens of the eye, the amount of strain of the intermediate portion 22I and the central portion 22C can be related to the elevation of protrusion 22CP. The decreased radial movement and decreased circumferential stretching of intermediate portion 22I can define an outer boundary of protrusion 22CP and encourage formation of protrusion 22CP.

The curvature profile elevation data and figures as described herein show that presbyopia can be treated with an appropriately sized support 100 coupled to intermediate portion 22I so as to produce a protrusion to treat presbyopia, and that the protrusion can be used in combination with additional components of accommodation, such as movement anteriorly of the intermediate portion 22I and the central portion 22C when the eye accommodates, and radially inward elastic force and radially inward movement of the peripheral portion of the lens capsule. The elastic peripheral and outer portions of the lens capsule can move the intermediate and central portions of the lens capsule anteriorly when the eye accommodates, and the elastic peripheral and outer portions of the lens capsule can provide radially inward force and radially inward movement of the peripheral portion of the lens capsule to move the intermediate portion 22I and the peripheral portion 22P anteriorly. The intermediate portion 22I can be coupled to stiffening support 100 with an amount of strain so as to provide appropriate far vision refraction and increased accommodation. The amount of strain of the stiffened intermediate portion may correspond to the stretched lens capsule for far vision, the non-stretched accommodating lens capsule, or amounts of strain in between corresponding to intermediate vision. In many embodiments, the intermediate portion 22I is stiffened when the eye does not accommodate and the lens capsule is stretched, for example when dilated during surgery, such that the intermediate portion 22I and the central portion 22C comprise a curvature and strain corresponding to the non-accommodating stretched lens capsule for far vision of the eye. Alternatively, the intermediate portion 22I can be stiffened with amounts of strain corresponding substantially to the non-stretched capsule when the eye accommodates, for example, such that the intermediate portion 22I and the central portion 22C comprise a curvature and strain corresponding to the non-stretched accommodating lens capsule.

FIGS. 2F and 2G show the support coupled to the anterior lens capsule having a light absorbing material such that the support appears as the pupil when the iris 16 slides over the support during constriction and dilation of the pupil. The support may comprise a thickness such that the pupil can slide over the support. For example, the support may comprise a thickness of no more than about 500 um, such as about 100 um or less, for example 30 um. The pupil can dilate with dim viewing conditions as shown in FIG. 2F and slide over the support. With dim viewing conditions the support may comprise an aperture of the eye to increase depth of field. Although a portion of the support may not be covered by the pupil, the support may comprise a light absorbing material such that the pupil appears dark and as the pupil and may not be readily perceptible by a person looking at the patient. With increased illumination the iris can constrict and slide over the support as indicated in FIG. 2G. With bright viewing conditions the iris may slide over the support 100 so as to cover the support 100 such that iris 16 defines the viewing aperture of the eye.

FIG. 2H shows the support comprising an inclined surface corresponding to a radius of curvature of the lens capsule to couple to the lens capsule. The capsule of the lens may comprise a curvature, and the surface of the support can be inclined relative to axis 11. The support 100 may comprise a concavely curved surface to contact capsule 42, for example to adhere to capsule 42. The capsule may comprise a radius R, and the support can be inclined at an angle 118 corresponding to the radius of the capsule. The support 100 may comprise thickness 110 such that the iris can slide over the support, as described herein. The support 100 may comprise a shape profile 117 comprising a rounded portion having the thickness 110 and extending to a chamfer at the inner and outer edges of the support such that the iris can slide over the support when coupled to the capsule. The support may comprise sufficient rigidity such the that the support comprises the inclined surface corresponding to the radius of the capsule when the support is expanded following insertion as described herein. Alternatively, the support may comprise a sufficiently flexible material cut or molded with the dimensions described herein such that the support can lay flat substantially along a flat surface prior to insertion and flex and bend to fit the curvature of the lens when adhered to the lens.

The oval support 100 can be used to correct one or more of many types of astigmatism of the eye, such as lenticular astigmatism, or corneal astigmatism, or combinations thereof.

FIG. 2I shows a view along the axis 11 of the eye having the stiffening support 100 coupled to the intermediate portion 22I comprising an annular oval shape to correct astigmatism of the eye. The annular oval shape profile of support 100 may comprise one or more of an elliptical shape, a lentoid shape, or an asymmetrical elliptical shape, extending substantially around central portion 22C such that protrusion 22CP comprises a substantially toric shape when the eye accommodates to as to correct the astigmatism of the eye. The astigmatism of the eye may comprise lenticular astigmatism or corneal astigmatism. For example, the astigmatism may comprise corneal with the rule astigmatism corresponding to a toric corneal shape having a steeper corneal curvature along a substantially vertical axis 12C and a flatter corneal curvature along a substantially horizontal axis 12B, such that a depth contour plot of the toric cornea shows ellipses such as ellipse 12A having a short axis extending along vertical axis 12C and long axis 12B perpendicular vertical axis 12C. Merely by way of example, the curvature of the cornea along axis 12B can correspond to an optical power of about 43 D, and the curvature of the cornea along axis 12C can correspond to an optical power of about 44 D, for example.

The long dimension of the oval annular support 100 can be aligned with the astigmatism of the eye such as with the rule astigmatism, so as to correct the vision of the eye. For example, the long dimension of the oval annular support 100 can be aligned with the steeper substantially vertical axis 12C, and the shorter dimension of the support 100 can be aligned with the flatter substantially horizontal axis 12B. The oval protrusion 23P can have a ratio of the long axis to the short axis so as to correct the astigmatism of the eye when the lens capsule is relaxed with ciliary muscle contraction and the eye accommodates for near vision, or when the lens capsule is stretched with the zonules and the ciliary muscle is relaxed for far vision.

The stiffened intermediate portion 22I coupled to the oval annular support 100 can induce astigmatism of the lens with toric protrusion 22CP so as to correct the astigmatism of the eye. The oval intermediate portion 22I coupled to annular oval support 100 comprises a shorter inner dimension 112A and a shorter outer dimension 114B. The oval stiffened intermediate portion 22I comprises an elongate inner dimension 112B and an elongate outer dimension 114B. The shorter inner dimension 112A and the elongate inner dimension 114A can define the oval outer boundary of the central portion 22C, such that the central portion 22C comprises an oval shape profile having one or more of an elliptical shape profile, a lentoid shape profile, or an asymmetrical elliptical shape profile. In many embodiments, the oval shape profile corresponds to a toric shape of the protrusion 22CP when the eye accommodates. When the lens capsule moves anteriorly with accommodation of the lens capsule such that central portion 22C comprises protrusion 22CP, the curvature change of the lens capsule can be related to the inner dimensions across the intermediate portion such as shorter inner dimension 112A and elongate inner dimension 112B. The shorter dimension 112A corresponds to a steeper curvature change of the lens capsule when the central portion moves anteriorly, and the elongate dimension 112B corresponds to a less steep change in curvature when the lens capsule moves anteriorly. The flatter curvature change along the axis of the elongate dimension 112B of the oval can correct the with the rule astigmatism along the vertical axis 12C.

The curvature 22CPC and corresponding elevation profile of the protrusion 22CP can be combined with the shorter inner dimension 112A and the elongate inner dimension 112B so as to determine the amount of optical correction of the protrusion. Alternatively or in combination, the ratio of the shorter dimension to the longer dimension and the elevation of the protrusion 23C can be used to determine the optical correction of the toric protrusion. For example, a patient can have corneal astigmatism with keratometer readings of about 43 D along an axis 180 of degrees and 44 D along an axis of 90 degrees corresponding to a refraction of the eye of about 0 D sphere–1.0 cylinder along an axis of 180 degrees. The dimensions of the short dimension and the long dimension of the oval can be sized to induce astigmatism of the lens to correct the astigmatism of the eye when the eye accommodates. For example the long dimension and the short dimension of the oval support can be sized such that the long dimension corresponds to about +1 D of optical power along axis 12C and the short dimension of the oval corresponds to about +2 D of optical power along axis 12B when the eye accommodates, such that the refraction of the eye with accommodation based on the change in curvature 22CPC of the central potion 22CP is about –2 D along axis 12B and about –2 D along axis 12C.

The cylinder of the eye can be corrected with many ratios of the long and short dimensions of the oval support 100. For example, an eye having a far vision refraction of 0 D sphere –1 D cylinder at axis of 180 degrees can be corrected with the oval protrusion. The long inner dimension 112B can be aligned along the 90 degree axis and the short inner dimension 112A can be aligned along the 180 degree axis. When the protrusion elevation height is about 50 microns, the oval support may have a long dimension of about 6 mm and a short dimension of about 4.2 mm, as described above with reference to FIG. 2A-3. Many additional combinations of dimensions can be identified by a person of ordinary skill in the art based on the teachings described herein. The protrusion coupled to the oval support can provide about +2 D of optical power along axis 12B and about +2 D of optical power along axis 12C corresponding spherical near vision refraction of about –2 D sphere when the eye accommodates.

As the central and intermediate portions of the anterior lens capsule can move forward together so as to provide optical correction in addition to the curvature 22CPC of the protrusion 22CP, the amount of accommodation and corresponding near vision refraction of the eye can be greater than the amount provided by the curvature 22CPC of protrusion 22CP. Alternatively or in combination, the intermediate portion 22I may be coupled to support 100 so as to provide additional stretching of the outer portion 22O and peripheral portion 22P of the lens capsule as described herein, such that the accommodation can be further increased. Based on the teachings described herein, a person of ordinary skill in the art can conduct additional experiments and computer simulations so as to determine empirically the protrusion height and corresponding sizes and ratios of the short axis and the long axis so as to correct astigmatism when the eye accommodates.

As a small amount of astigmatism can be tolerated by the patient, the oval support can be used to increase the amount of accommodation of the eye and provide a small amount of astigmatism with acceptable vision, for example about 1 D astigmatism or less.

FIGS. 2J and 2K show side and end views, respectively, of the support comprising a narrow profile configuration 120 for insertion into the eye through an incision in the cornea. The support in configuration 120 can be inserted through an incision of no more than about 2 mm, for example. The support may comprise a foldable flexible portion 122, for example, that can be unfolded when the support is expanded to the wide profile configuration as described above and adhered to the lens capsule.

FIGS. 2L and 2M show the support 100 comprising an expanded wide profile configuration, and narrow profile configuration 120 for insertion into the eye through an incision in the cornea, respectively. The support in configuration 120 can be inserted through an incision of no more than about 2 mm, for example. The wide profile configuration may comprise an annular structure, such as a ring or oval annular structure such as a C-ring annular structure. The support 100 can be twisted for insertion through the incision in the narrow profile configuration 120 and can expand to the wide profile configuration and adhered to the lens capsule as described herein. The C-ring annular structure may be aligned with the lens capsule so as compensate for broken zonules, for example.

FIG. 2M1 shows a narrow profile configuration for insertion into the eye through the incision with rotation of the support 100 shown in 2L.

Figure 3A:
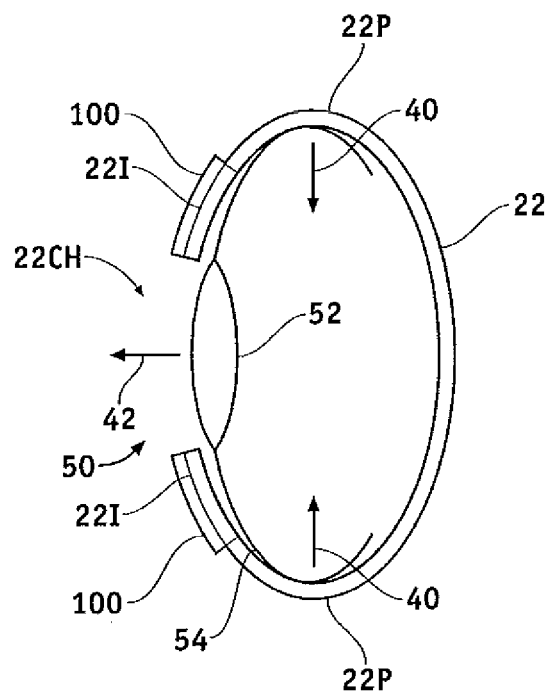
FIG. 3A shows a side view the eye having an accommodative IOL positioned substantially within a lens capsule having the intermediate portion of the capsule stiffened with the support to increase accommodation, in accordance with embodiments of the present invention.
Figures 1, 3A:
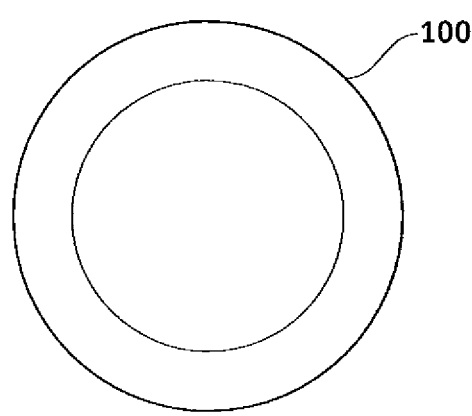

FIG. 3A shows a side view the eye having an accommodating IOL 50 positioned substantially within a lens capsule having the intermediate portion coupled to support 100 to stiffen the intermediate portion and increase accommodation. The accommodating IOL 50 comprises a lens 52 and a haptic 54. The inward force of the capsule in contact with haptic 54 as indicated with arrow 40 can move the lens 52 forward to increase optical power of the eye and increase the amount of accommodation of the accommodating lens 50.

FIG. 3A1 shows the support 100 as in FIG. 3A suitable for use with an accommodative IOL. The support for the accommodative IOL can be similar to the support used with the central portion of the lens capsule, and may comprise the substantially annular structure, such as the ring shaped structure or the C-shaped structure as described herein, for example The accommodating IOL 50 may be placed at least partially within the capsule 22. A capsulorhexis surgery may comprise removal of the central optical portion of the anterior lens capsule, for example during cataract surgery, and the tissue of the intermediate portion 22I can be stiffened with the support so as to couple to the intermediate portion and the draw the peripheral portion inward with accommodation as indicated by arrow 40. The coupling of the support to the intermediate portion 22I decreases radial motion of the intermediate portion 22I so as to couple to the peripheral portion with such that the peripheral portion can move the haptic radially inward with force as indicated with arrow 40. The coupling of the stiffening support 100 to the intermediate portion 22I can be performed before, during or after the capsulorhexis, or combinations thereof. For example, the intermediate portion 22I of the anterior capsule can be coupled prior to capsulorhexis such that the curvature and strain of the lens capsule can be maintained. The support can be coupled to the intermediate portion such that the strain and radial position of the intermediate portion correspond to the relaxed capsule of the eye accommodating for near vision, for example. Alternatively or in combination, the support can be coupled with the pupil dilated such that the curvature of natural lens capsule is maintained for far vision, and such that the curvature and strain of the intermediate portion corresponds to the curvature and strain of the stretched lens capsule of the eye. Alternatively or in combination, the intermediate portion can be coupled after capsulorhexis. Following capsulorhexis, a second support can be positioned on the intermediate portion of the posterior capsule as shown above, for example.

The accommodating IOL 50 may comprise one or more components of know accommodating IOLs. The lens 52 may comprise a rigid material that provides accommodation when the lens 52 moves anteriorly. Alternatively or in combination, the lens 52 may comprise a flexible material that moves and increases curvature when the eye accommodates. Example of lenses having components suited for use in accordance with embodiments as described herein include the Crystalens™ HD IOL, Focus IOL™ IOL, Synchrony IOL, and FlexOptic™ IOL.

The accommodating IOL 50 can be combined with the oval support as described herein. For example, the accommodating IOL 50 may comprise the flexible material that moves and increases curvature, and the oval support as described above can increase curvature of the accommodating IOL differentially so as to correct astigmatism of the eye.

Figure 3B:
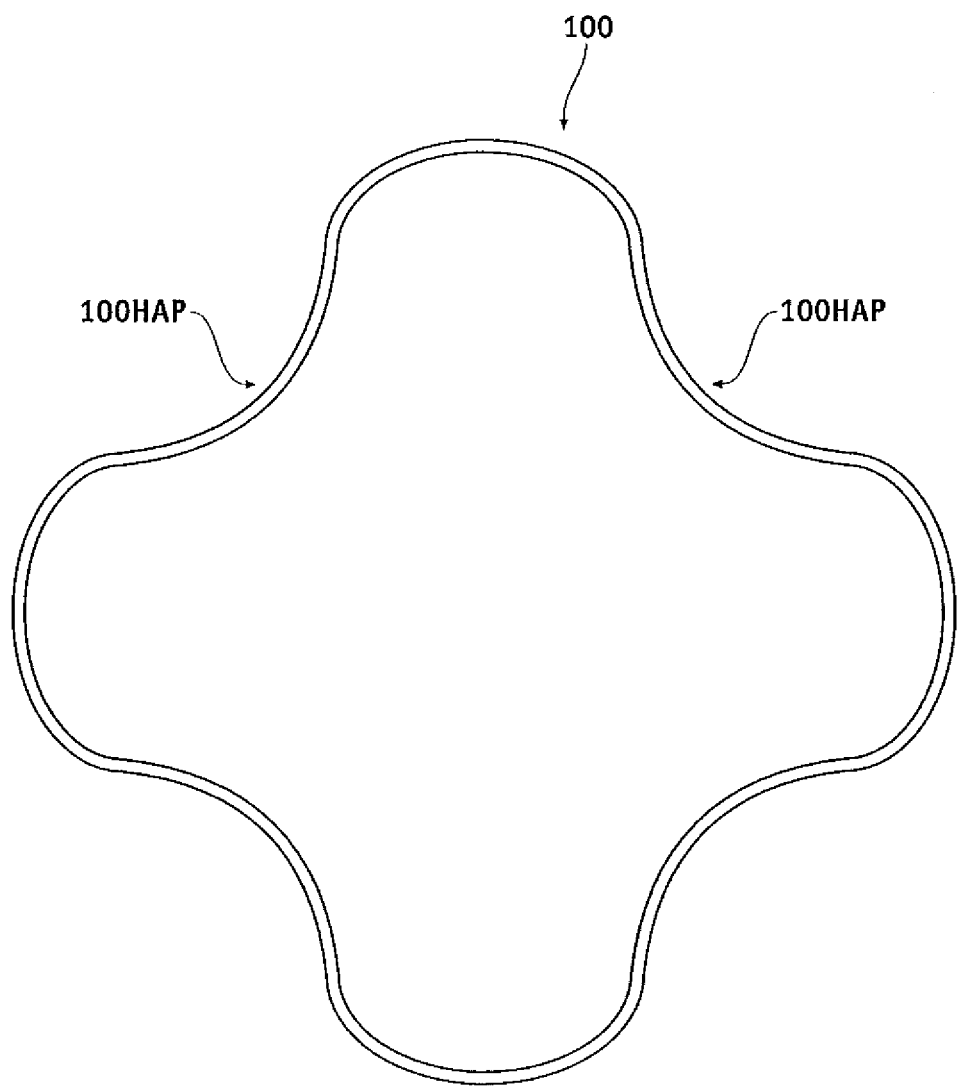
FIG. 3B shows support having structures comprising inwardly curved portions to couple to the haptic, in accordance with embodiments of the present invention.

FIG. 3B shows support 100 comprising structures comprising curved portions 100HAP to couple to the haptics 52 of the IOL. The structures to couple to the haptics may comprise a first structure comprising first curved portion to couple to a first haptic and second structure comprising a second curved portion to couple to a second haptic. The curved portions 100HAP may comprise inwardly curved portions that may focus force to each corresponding haptic. The support 100 may comprise an annular structure having a serpentine undulations extending circumferentially around the annular structure, for example comprising a wavy ring.

Figure 3C:
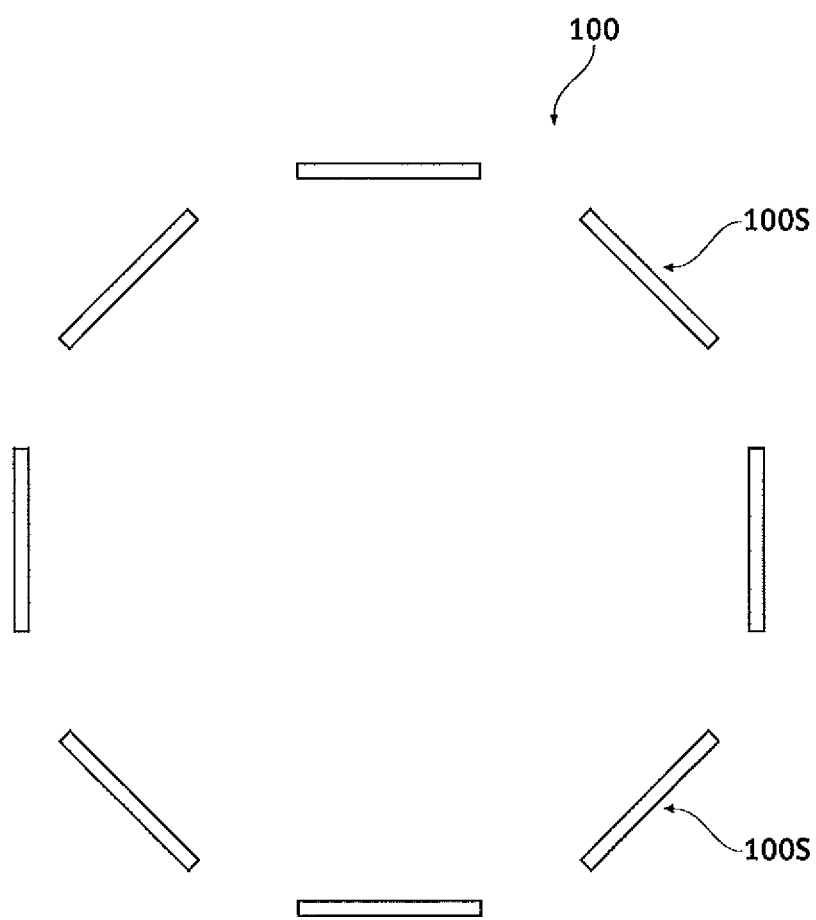
FIG. 3C shows the support comprising a plurality of elongate segments arranged so as to form support in situ on the lens capsule, in accordance with embodiments of the present invention.

FIG. 3C shows support 100 comprising a plurality of elongate segments 100S arranged so as to form support 100 in situ on the lens capsule. The plurality of elongate segments 100S can be passed through the incision together, or sequentially, or combinations thereof, and adhered to the intermediate portion of the lens capsule to increase accommodation. The plurality of elongate segments may comprise substantially straight segments, or curved segments that can be arranged to increase accommodation. The plurality of segments can be used to increase forces on the haptics 52, compensate for broken zonules, or correct astigmatism in the lens, and combinations thereof. For example, the plurality of segments 100S can be arranged in an oval to correct astigmatism as described herein. The plurality of segments can be adhered to the lens capsule with an adhesive as described herein. In many embodiments, each segment of the plurality is aligned with one of the haptics 52. For example, for an accommodating IOL with eight haptics, eight elongate segments can be adhered on the lens capsule in an octagonal configuration such that each elongate segment corresponds to one of the haptics.

Figure 3D:
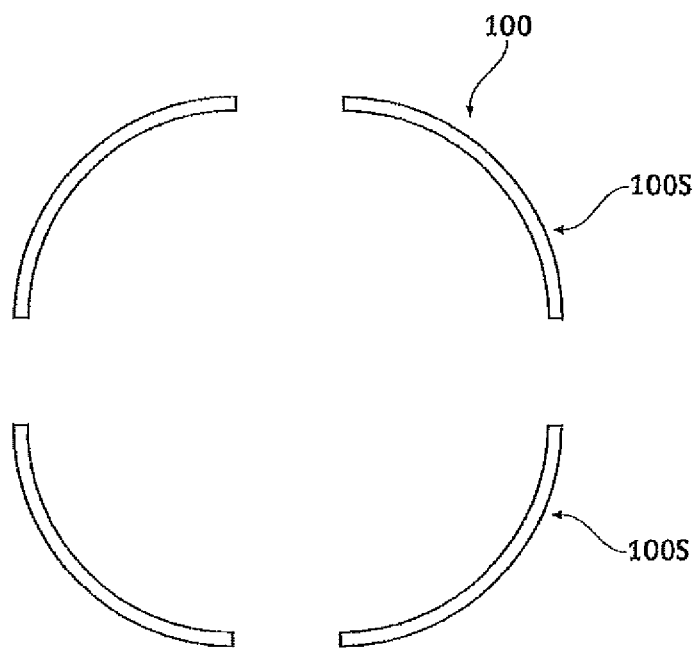
FIG. 3D shows the support comprising a plurality of curved elongate segments arranged so as to form support in situ on the lens capsule, in accordance with embodiments of the present invention.

FIG. 3D shows the support 100 comprising a plurality of curved elongate segments 100S arranged so as to form support in situ on the lens capsule. The plurality of curved elongate segments may comprise segments that curve along the elongate dimension so as to approximate a circle, or annular oval, when placed on the eye. Each segment of the plurality can be aligned with one of the haptics 52. For example, for an accommodating IOL with four haptics, four curved elongate segments can be adhered on the lens capsule in an circular configuration such that each elongate segment corresponds to one of the haptics. The spacing between the curved elongate segments can vary to treat astigmatism of the eye. Alternatively or in combination, each of the curved elongate segments 110S may comprise a portion of an ellipse aligned with cornea so as to treat astigmatism as described herein.

Figures 1, 2, 3E:
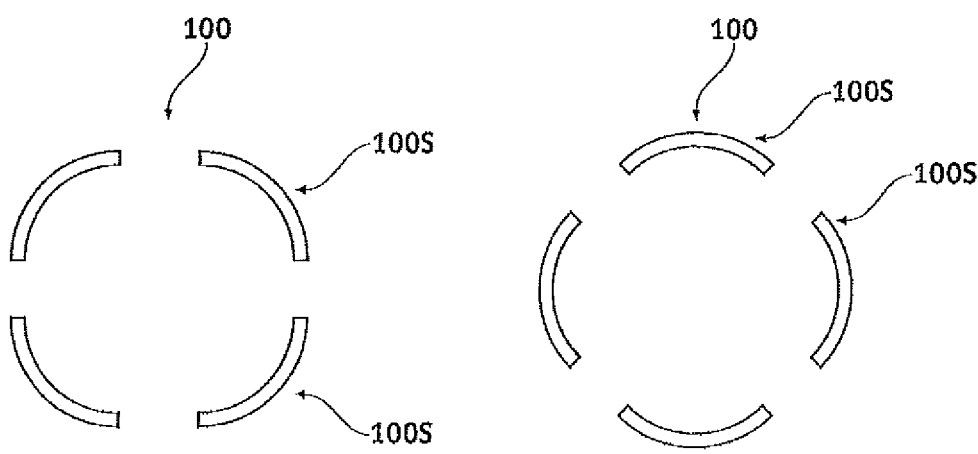

FIGS. 3E1 and 3E2 show plurality of curved elongate segments aligned on the anterior lens capsule and posterior lens capsule, respectively, so as to vault the lens capsule and increase accommodation. The plurality of curved elongate segments can be used on both the posterior capsular bag and the anterior capsular bag. For example, a first plurality of curved elongate segments can be inserted after the natural lens is removed, and before the IOL is implanted, and a second plurality of curved elongate segments inserted and adhered on the anterior lens capsule, with the first plurality rotationally offset from the second plurality so as to encourage vaulting of the lens capsule. The rotation of the first plurality relative to the second plurality can provide anterior vault during accommodation and posterior vault during non-accommodation, which can increase and amplify the accommodative range of the IOL.

Figure 4A:
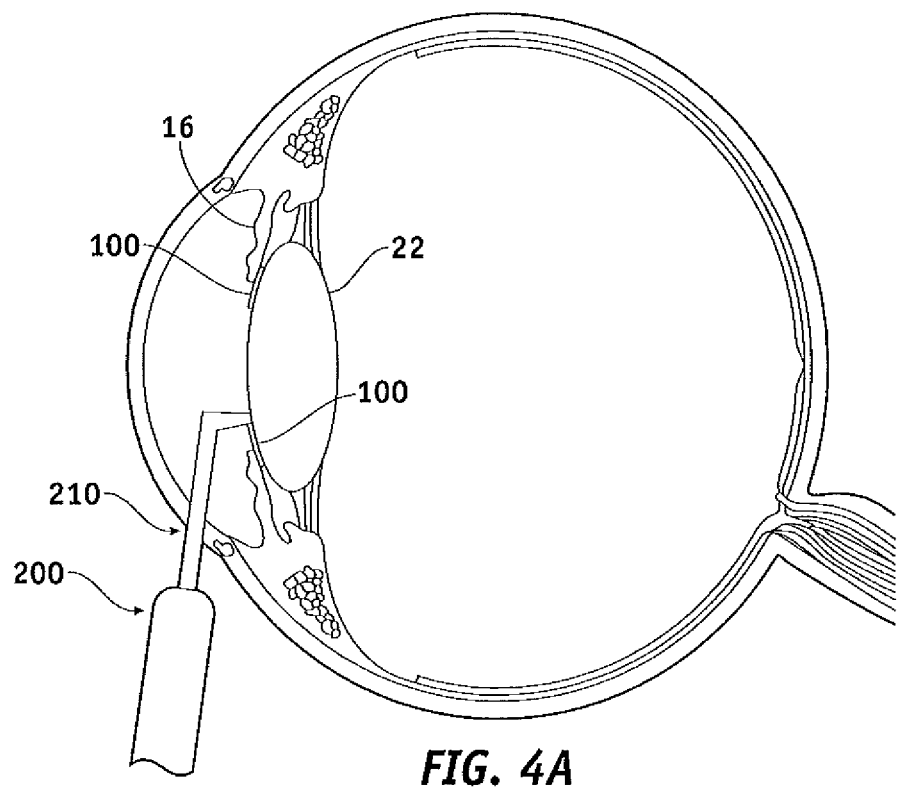
FIG. 4A shows a side view of a capsulorhexis treatment of the eye to remove a central portion of the lens capsule in which the support guides the capsular tissue cutting, in accordance with embodiments of the present invention.

FIG. 4A shows a side view of a capsulorhexis treatment of the eye to remove a central portion of the lens capsule in which the support 100 guides the capsular tissue cutting. The support can be used to guide cutting with many tissue cutting devices such as lasers and probes. For example probe 200 can be configured to cut tissue of capsule 42. The distal portion of probe 200 can fit through incision 210 in the cornea to cut the capsule.

Figure 4B:
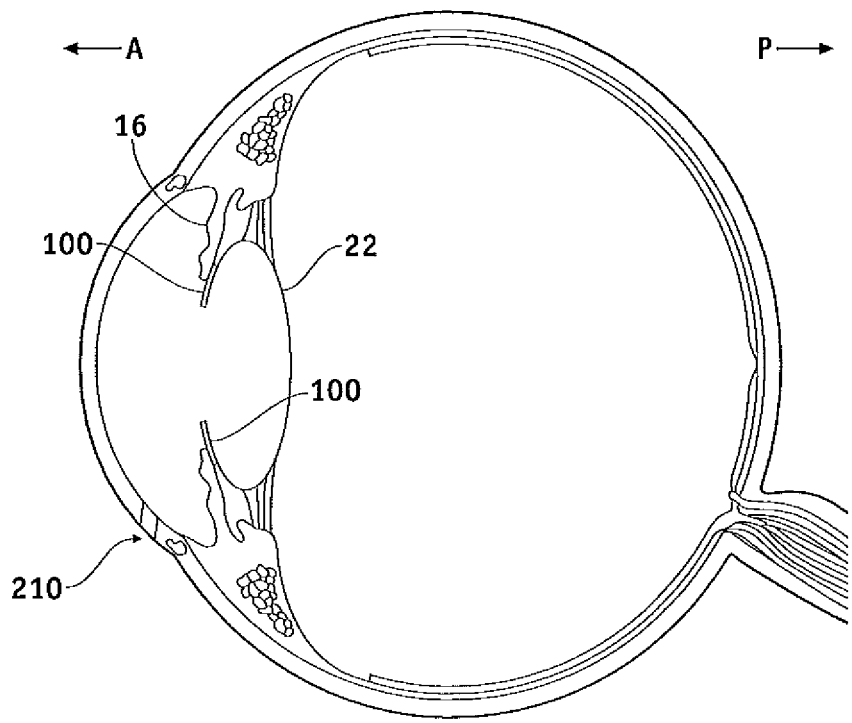
FIG. 4B shows a side view treatment of the eye having the central portion of the anterior capsule removed such that the eye is ready to receive an accommodating IOL, in accordance with embodiments of the present invention.

FIG. 4B shows a side view treatment of the eye having the central portion of the anterior capsule removed such that the eye is ready to receive an accommodating IOL. In many embodiments, a second support can be positioned on the posterior capsule, for example passed through the first support in the narrow elongate configuration as described above and expanded to the wide profile configuration at least partially within the capsule.

As the tissue strain of the intermediate portion of the capsule coupled to the support may be related to both the far vision refraction and accommodation of the eye, an adjustable support can be used to adjust one or more of the far refraction of the eye or the amount of accommodation of the eye.

Figure 4C:
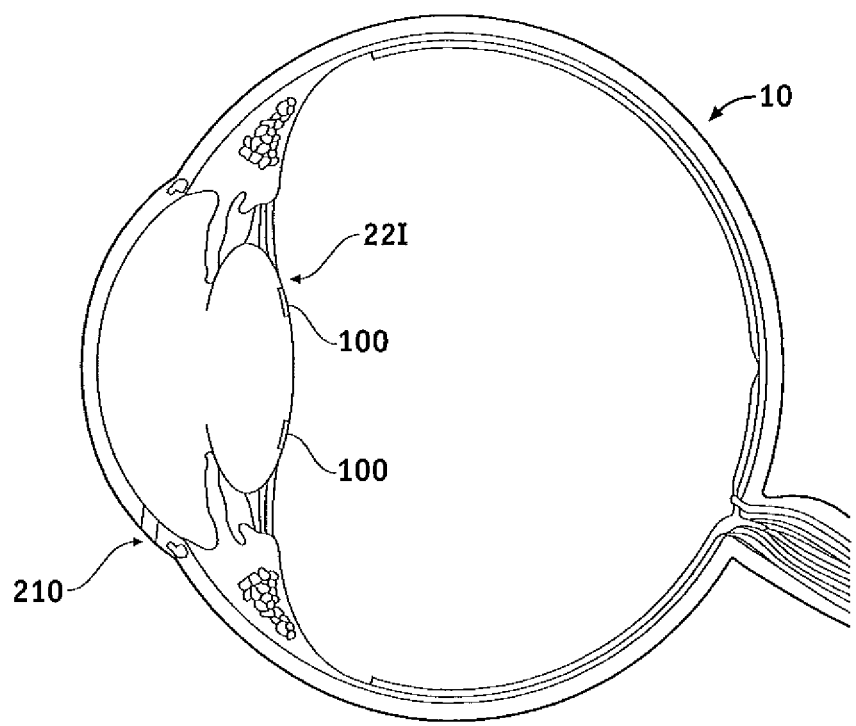
FIG. 4C shows a side view of a support positioned on the posterior capsule following capsulorhexis to remove a central portion of the lens capsule, in accordance with embodiments of the present invention.

FIG. 4C shows a side view of support 100 positioned on the posterior capsule following capsulorhexis. The dimensions of the support can be sized larger than the capsulorhexis diameter such that the support can be moved through the edge of the cut lens capsule with at least some stretching of the lens capsule. Alternatively or in combination, the support 100 can be expanded from the narrow profile configuration to the wide profile configuration at least partially within the lens capsule.

Figure 4D:
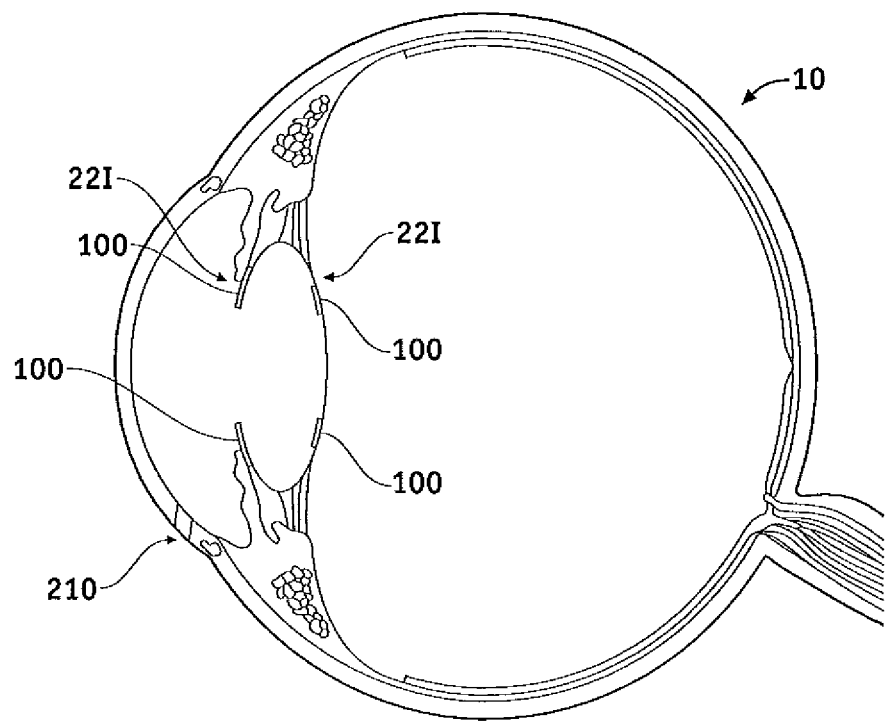
FIG. 4D shows a side view of a first support positioned on the anterior capsule and a second support on the posterior capsule after capsulorhexis, in accordance with embodiments of the present invention.

FIG. 4D shows a side view of an anterior support 100 positioned on the anterior capsule and a posterior support 100 positioned on the posterior capsule after capsulorhexis. The anterior support 100 can be positioned on the anterior lens capsule after the posterior support 100. The accommodating IOL can be inserted when the anterior support 100 and the posterior support 100 are coupled to the intermediate portion of the lens capsule. Alternatively, the lens can be placed at least partially in the lens capsule when the posterior support is positioned on the posterior capsule and before the anterior support is positioned on the anterior capsule.

Figure 5A:
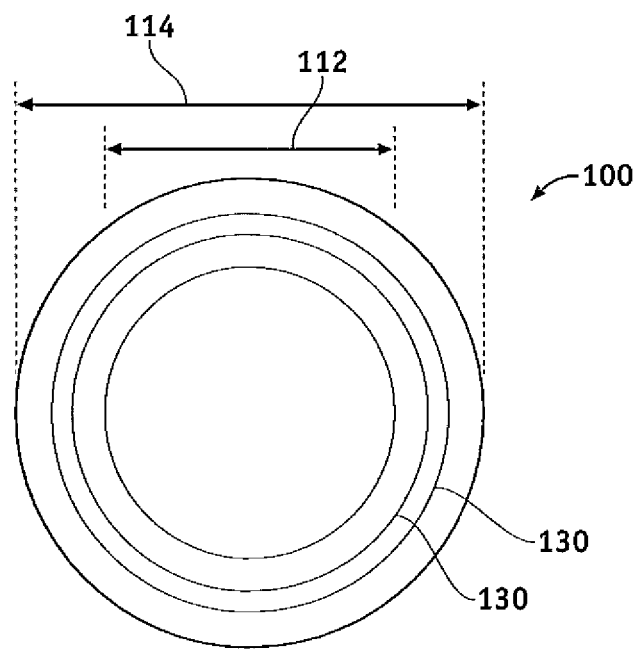
FIG. 5A shows a top view of a support comprising at least one structure to adjust the support, in accordance with embodiments of the present invention.

FIG. 5A shows a top view of a support comprising at least one structure 130 to adjust the support. The at least one structure may comprise a layer of material disposed in an annular pattern on the support, for example.

Figure 5B:
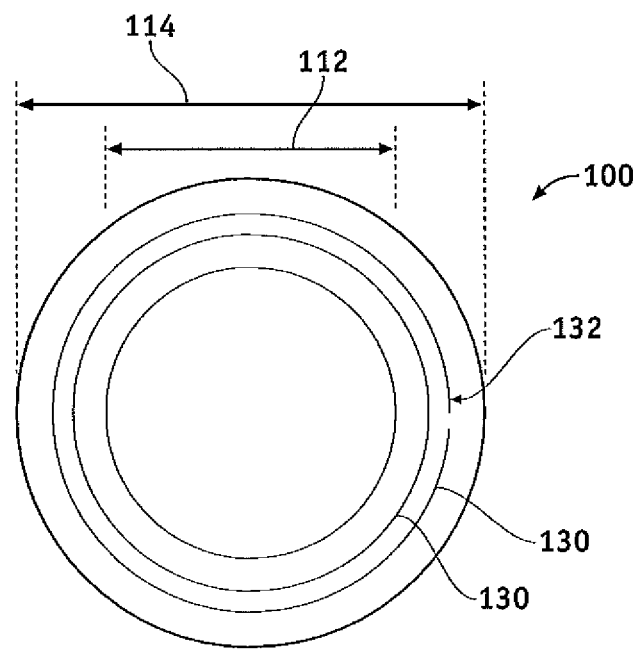
FIG. 5B shows a top view of the structure as in FIG. 5A with one of the at least one structures cut to adjust the support, in accordance with embodiments of the present invention.

FIG. 5B shows a top view of the structure as in FIG. 5A with a cut component 132 of the at least one structure to adjust the support. The component of the support can be cut in many ways, for example with light energy such as a laser light energy from a pulsed laser such as an Nd:YAG laser or a femtosecond laser, for example. The adjustable support can be configured so to adjust one or more of far vision refraction, accommodation, or astigmatism of the eye. The dimension across the support, for example the inner annular diameter 112 and the outer annular diameter 114, can be adjusted radially inward so as to increase strain on the outer portion of the capsule and increase force of the lens capsule such that the far vision refraction of the eye can be adjusted toward nearsightedness, or accommodation can be increased, or combinations thereof. Alternatively, the dimension across the support can be adjusted radially outward so as to decrease strain on the outer portion of the capsule and decrease force of the lens capsule such that the far vision refraction of the eye can be adjusted toward farsightedness, or accommodation can be decreased, or combinations thereof. The support can be adjusted from a circular profile to an oval profile to correct astigmatism as described above. The support may comprise an oval profile configuration as described above, and the ratio of the short dimension of the oval to the long dimension of the oval can be adjusted to correct the astigmatism of the eye.

The adjustable support having the at least one structure 132 may comprise one or more of many components so as to adjust the support. The support may comprise a shape changing material to adjust the dimension across the support when the support is treated with energy. The shape changing material may comprise a heat sensitive material to stiffen the support when the support is coupled to the intermediate portion. The shape changing material comprises one or more of a metal or a polymer.

The adjustable support may comprise a polymer such as an elastomeric material, for example, and the at least one structure may comprise a plurality of metal bands deposited in layers on the support, for example, such that cleavage of one of the structure can adjust the support radially. The at least one structure 130 of the adjustable support may comprise layers of polymer, and the layers of polymer can be arranged in a progressively stiffer membrane arrangement, such that inner layers comprise more stiffness than outer layers. An inner layer of the at least one structure 132 can be severed so as to release an amount of contractual force so as increase the dimension across the support. Alternatively, the at least one structure may comprise a second component having pre-loaded configuration opposite a first component comprising inner layer, such that cutting of the first component of the at least one structure allows the second component to move the support inward radially and decrease strain of the intermediate portion such that the dimension across the intermediate portion is decreased and so as to increase stretching and corresponding force of the outer portion of the lens capsule. The decrease in dimension across the intermediate support may adjust the far refraction of the eye toward myopia, for example, and may increase accommodative force so as to provide increased amounts of accommodation, for example.

Figure 6A:
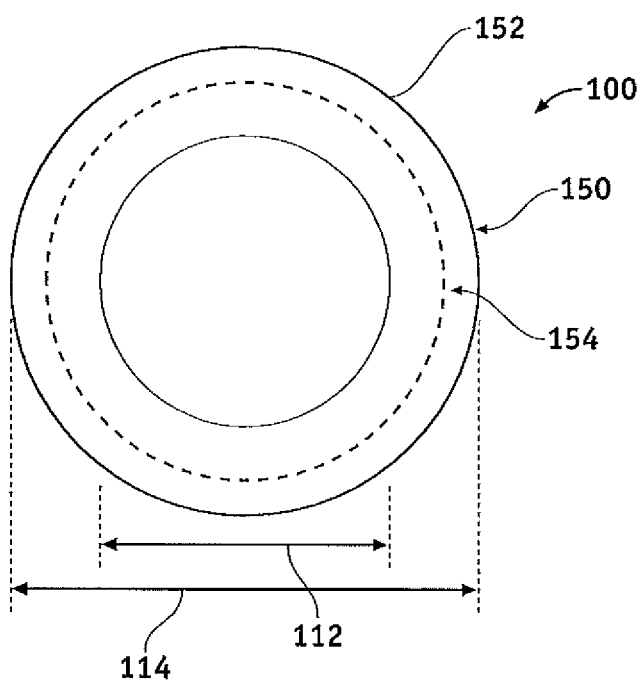
FIGS. 6A and 6B show a top view and a side view, respectively, of the support comprising protrusions defining a channel to receive the lens capsule to couple the support to the lens capsule, in accordance with embodiments of the present invention.
Figure 6B:
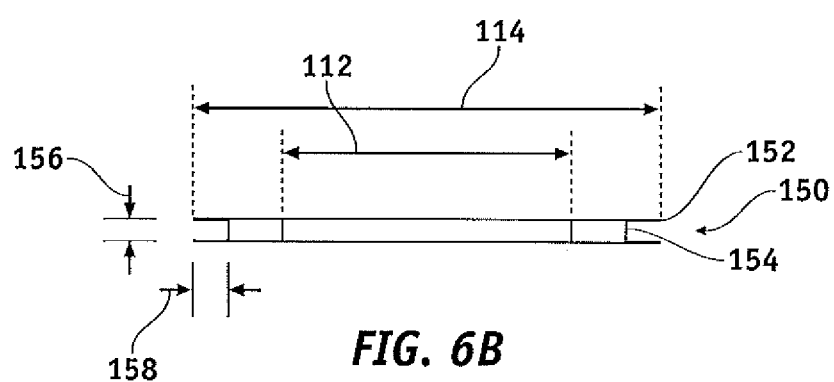

FIGS. 6A and 6B show a top view and a side view, respectively, of the support 100 comprising protrusions 152 defining a channel 154 to receive the lens capsule to couple the support to the lens capsule. The support comprises a structure 150 having protrusions 152 separated by an inner distance 156 sized to receive the intermediate portion of the lens capsule. The inner distance 156 can be from about 30 to about 500 um. The protrusions 150 may comprise rims extending circumferentially around the support, in which each rim has an inner surface to contact the portion of the capsule, and the distance 158 extends between the inner surfaces of the rims. The protrusions can extend outward a distance 158 to receive the intermediate portion of the lens capsule and couple to the lens capsule with mechanical coupling as described herein. The mechanical coupling may comprise one or more of clamping, locking, threads, bayonet mounting or mechanical force. For example, the protrusions may comprise tabs that can be moved together to clamp the lens capsule. The inner annular diameter 112 and the outer annular diameter 114 may comprise dimensions of an oval as described herein.

Experimental and Computer Modeling

Figure 7:
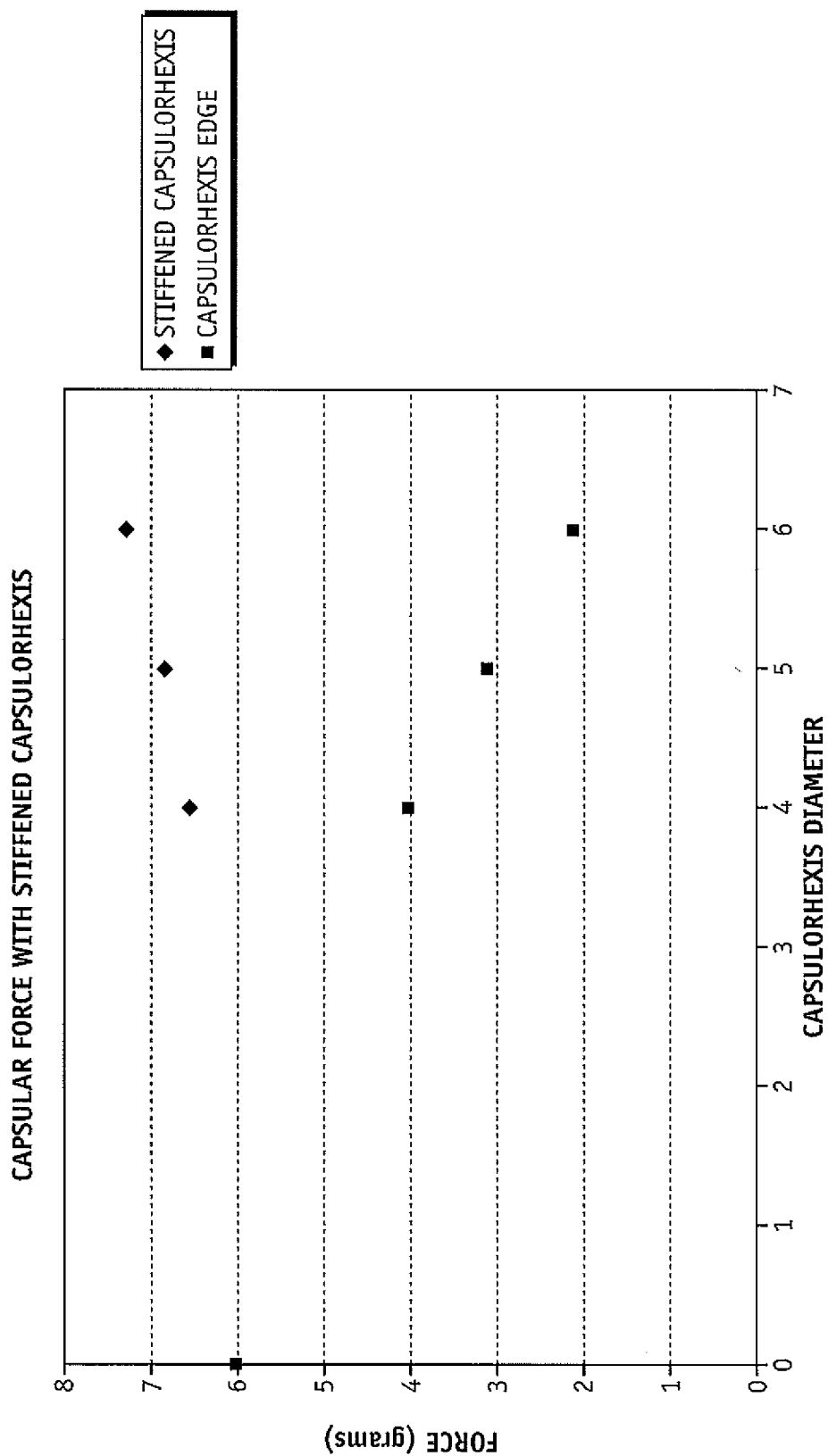
FIG. 7 shows a graph of accommodative force of the peripheral portion of the lens with the support coupled to the intermediate portion based on calculations.

FIG. 7 shows a graph of radial accommodative force of the peripheral portion of the lens capsule with the support coupled to the intermediate portion based on calculations. The radial force was determined using finite analysis and known material properties and geometries of the lens capsule. The finite element modeling used Abaqus™ software commercially available from Simulia of Providence, R.I.

The capsule was modeled with finite element shells having a uniform thickness of about 30 um. The intermediate portion of the lens capsule corresponding to the location of the support was constrained such that the radial position remained fixed but was allowed to move along the axis of the coordinate system, as described herein. The force profile of the lens capsule for the normal lens was scaled to be about 6 g. The lens profile in the non-stretched lens condition corresponding to accommodation was used to determine the fixed radial position of the lens capsule corresponding to the location of the support. This fixed radius condition corresponds to placement of the ring when the eye accommodates, for example adhering the ring to the eye when the eye accommodates. Alternatively or in combination, the tissue can be coupled to the stiffening support 100 such that the radial distance of the intermediate portion is fixed at a radial distance corresponding to an at least partially stretched lens capsule, for example. The support 100 can be adjusted, and may comprise a ring adhered to the eye when dilated and adjusted as described herein. Although the initial determined force was somewhat higher for the normal lens capsule, for example about 30 g, this elevated force can be related to modeling of the lens capsule with uniform thickness. Based on the teachings described herein, a person of ordinary skill in the art can model the lens capsule with varying thickness and material properties to determine the force profile for the stiffening ring.

With the non-stiffened capsulorhexis, the inward force of the lens capsule corresponding to accommodation decreased to about 4, 3 and 2 grams with capsulorhexis diameters of 4, 5 and 6 mm respectively. With the stiffened capsulorhexis having the fixed radius of the capsulorhexis edge corresponding to a rigid support coupled to the intermediate portion of the lens capsule, the inward force of the lens capsule corresponding to accommodation increased to 6.5, 6.8 and 7.2 grams, with capsulorhexis diameters of 4, 5 and 6 mm respectively.

The unexpected result of these calculations indicate that stiffening of the intermediate portion of the capsule with the support as described herein can increase accommodative force following capsulorhexis as compared to non-stiffened capsulorhexis. These calculations also indicate that stiffening of the intermediate portion of the normal lens capsule can increase redistribute forces of the lens capsule so as to increase the amount of accommodation of the natural lens.

A person of ordinary skill in the art will recognize many adaptations and variations on simulations and calculations that can be performed so as to determine empirically the properties of the support and resulting accommodation of the lens capsule, such as finite element analysis, finite difference analysis, and dimensional analysis to determine the response of the lens to the support coupled to the intermediate portion as described herein.

Experiments and simulations can be performed to determine the profile of the support so as to stiffen the intermediate portion of the lens capsule. For example, additional studies can be performed to determine the affect of dilation when the support is adhered to the lens capsule, and effectiveness of adjusting the support to adjust refraction, for example.

Following experimental simulations in vivo measurement can be performed on living eyes. The change in refraction and accommodation can be measured so as to ensure that the amount of accommodation increases by at least about 1 D for at least about 3 months in a primate animal model and the refraction can be measured so as to ensure that the refraction changes by no more than about 2 D, for example no more than about 1 D with at least 1 D of increased accommodation, for example.

Clinical trials can be performed to determine the amount of accommodation increased with the tissue stiffening as described herein.

Based on the teachings described herein a person of ordinary skill in the art can determine the profile and modulus of the support and adhesives and structures suitable for coupling to the capsule so as to stiffen the intermediate portion of the capsule and increase accommodation.

While the exemplary embodiments have been described in some detail, by way of example and for clarity of understanding, those of skill in the art will recognize that a variety of modifications, adaptations and changes may be employed. Hence the scope of the present invention shall be limited solely by the claims.

What is claimed is:

1. An apparatus to treat a human eye having a lens, the lens having a capsule that is complete, the apparatus comprising:
    a support that is expandable comprises a first narrow profile configuration and a second wide profile configuration, the narrow profile configuration sized to pass through an incision, the wide profile configuration sized to extend substantially along an intermediate portion of the lens capsule to decrease radial movement of the intermediate portion and increase an amount of accommodation of the eye,
    wherein the support in the second configuration comprises an arcuate profile having an interior surface configured to directly contact an exterior-anterior surface of the lens capsule at only the intermediate portion thereof, thereby leaving a central portion of the lens capsule free to change curvature; and
    wherein the intermediate portion is disposed between a central optical portion that permits light to be transmitted through the pupil of the eye, and a peripheral portion attached to zonules of the eye.

2. The apparatus of claim 1, wherein the support comprises a modulus of at least 600 kPA such that the support decreases the radial movement of the intermediate portion when the eye accommodates.

3. The apparatus of claim 1, wherein the support comprises a thickness dimensioned such that the iris slides over the support when the iris contracts and dilates and wherein the support comprises a light absorbing material such that the support appears dark when the iris slides over the support.

4. The apparatus of claim 1, further comprising a biocompatible adhesive to adhere the support to the intermediate portion of the lens capsule.

5. The apparatus of claim 4, wherein the adhesive comprises one or more of adhesive comprising one or more of cyanoacrylate, temperature sensitive adhesive, thermoreversible adhesive, a curable adhesive, a patterned microstructure based adhesive, a glycoprotein based adhesive or a cross-linker such as a photosensitive crosslinker.

6. The apparatus of claim 1, wherein the support comprises an adjustable support in the second configuration such that a dimension across the support is adjustable to adjust one or more of a refraction of the eye for far vision or an amount of accommodation of the eye.

7. The apparatus of claim 6, wherein the support comprises a shape changing material to adjust the dimension across the support when the support is treated with energy.

8. The apparatus of claim 7, wherein the shape changing material comprises a heat sensitive material to stiffen the support when the support is coupled to the intermediate portion.

9. The apparatus of claim 7, wherein the shape changing material comprises one or more of a metal or a polymer.

10. The apparatus of claim 6, wherein the adjustable support comprises layers of polymer and wherein the layers of polymer are arranged in a progressively stiffer membrane such that inner layers comprise more stiffness than outer layers and wherein at least one inner layer is severed so as to release an amount of contractual force increase the dimension across the adjustable support.

11. The apparatus of claim 1, wherein the support comprises an annular oval shape profile having an inner boundary sized to extend substantially around the central portion and define the central portion with an oval outer boundary.

12. The apparatus of claim 11, wherein the oval support comprises an annular oval shape profile having an inner boundary sized to extend substantially around the central portion and define the central portion with an oval outer boundary.

13. The apparatus of claim 1, wherein the support comprises a structure having protrusions separated by a distance dimensioned to receive the portion of the lens capsule.

14. The apparatus of claim 13, wherein the structure comprises a channel and wherein the protrusions comprise rims extending circumferentially around the support, each rim having an inner surface to contact the portion of the capsule.

15. The apparatus of claim 1, wherein the support comprises a first portion having a first structure to couple to a first haptic and a second portion having a second structure to couple to a second haptic so as to focus force to the first haptic and the second haptic when the first portion is aligned with the first haptic and the second portion is aligned with the second haptic.

16. The apparatus of claim 1, wherein the support is configured to decrease spherical aberration of the eye.

* * * * *